(12) United States Patent
Metodiev

(10) Patent No.: US 9,310,371 B2
(45) Date of Patent: Apr. 12, 2016

(54) DETECTION AND TREATMENT OF CANCER

(71) Applicant: University of Essex Enterprises Ltd., Colchester (GB)

(72) Inventor: Metodi Vladimirov Metodiev, Colchester (GB)

(73) Assignee: University of Essex Enterprises Ltd., Colchester (GB)

( * ) Notice: Subject to any disclaimer, the term of this patent is extended or adjusted under 35 U.S.C. 154(b) by 0 days.

(21) Appl. No.: 14/055,396

(22) Filed: Oct. 16, 2013

(65) Prior Publication Data

US 2015/0104809 A1   Apr. 16, 2015

(51) Int. Cl.
  *G01N 33/68* (2006.01)
  *G01N 33/574* (2006.01)

(52) U.S. Cl.
  CPC .... *G01N 33/57492* (2013.01); *G01N 33/57484* (2013.01); *G01N 2440/14* (2013.01)

(58) Field of Classification Search
  None
  See application file for complete search history.

(56) References Cited

U.S. PATENT DOCUMENTS

2010/0081666 A1\* 4/2010 Coughlin et al. ........ 514/252.19
2010/0279316 A1\* 11/2010 Gorelik et al. ............... 435/7.21

OTHER PUBLICATIONS

Metodieva et al. (Neoplasia, 15(6): 660-668, Jun. 2013).\*

\* cited by examiner

*Primary Examiner* — Brad Duffy
*Assistant Examiner* — Nelson B Moseley, II
(74) *Attorney, Agent, or Firm* — Greer, Burns & Crain, Ltd.

(57) ABSTRACT

The present invention relates to a method for diagnosing, evaluating the prognosis of a cancer patient and evaluating the aggressiveness of a cancer. The methods comprise detecting the phosphorylation status of a Scribble protein, a fragment or variant thereof, wherein the phosphorylation status is indicative of cancer, prognosis and the aggressiveness of a cancer. In one embodiment the cancer is breast cancer.

13 Claims, 12 Drawing Sheets

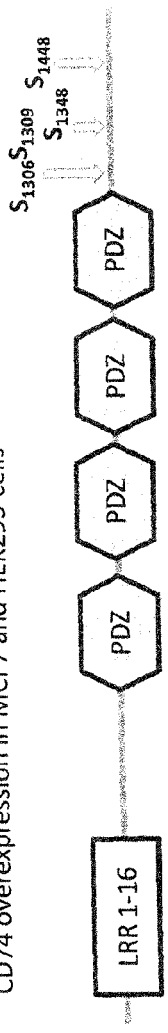
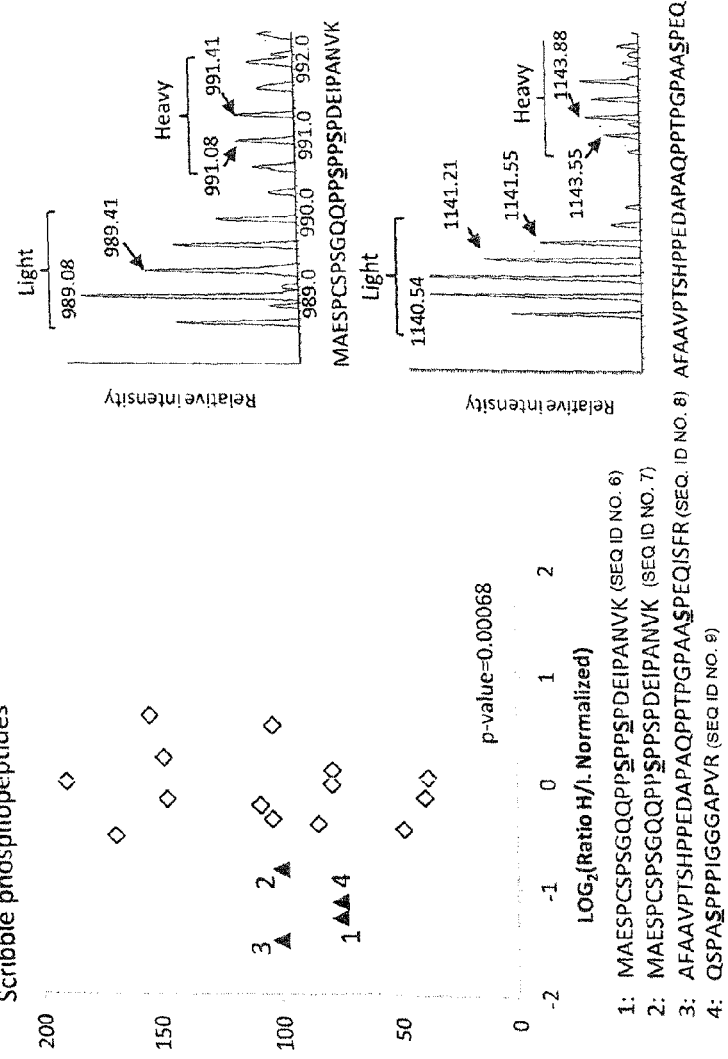
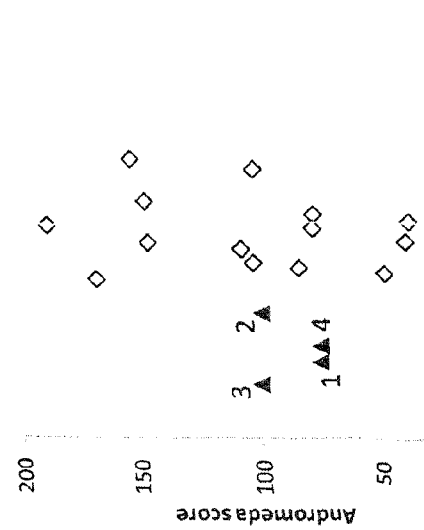

Figure 1A. Scribble serine phosphorylation hot spots affected by CD74 overexpression in MCF7 and HEK293 cells Figure 1B. Normalized H/L ratios for detected Scribble phosphopeptides 1: MAESPCSPSGQQPPSPPSPDEIPANVK (SEQ ID NO. 6)
2: MAESPCSPSGQQPPSPPPSPDEIPANVK (SEQ ID NO. 7)
3: AFAAVPTSHPPEDAPAQPPTPGPAASPEQISFR (SEQ ID NO. 8)
4: QSPASPPPIGGGAPVR (SEQ ID NO. 9)

Figure 1C. High-resolution MS scans

Figure. 3
A Western blotting analysis  B FACS analysis
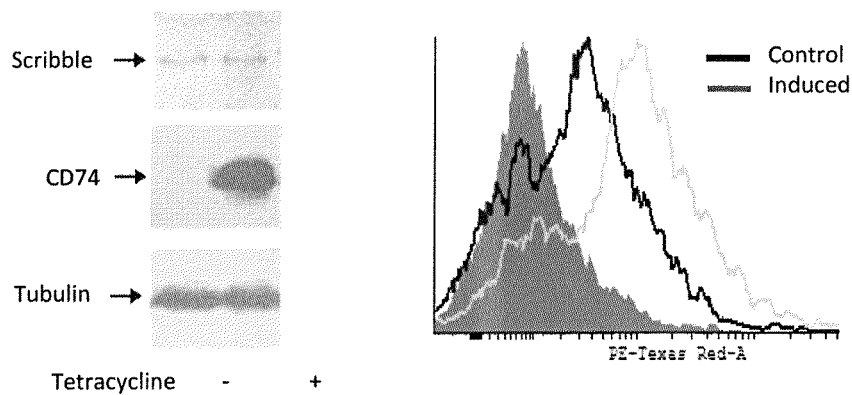
C Indirect immunofluorescence analysis
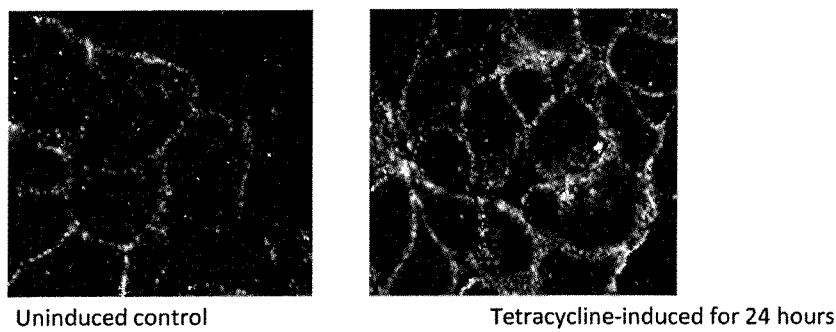

Figure 6
IHC staining of CD74 in TNBC
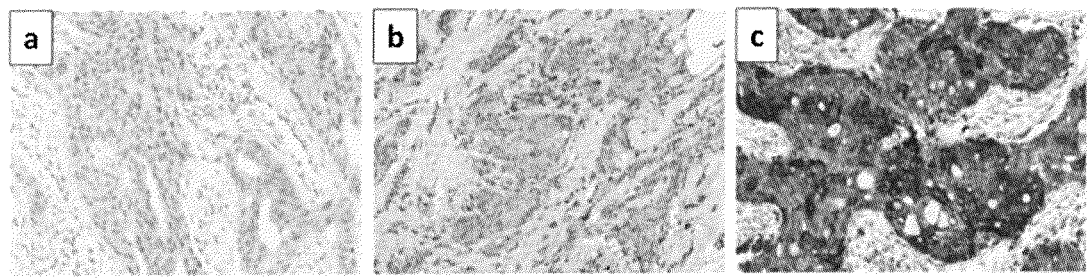
IHC staining of CD74 in 14 TNBC specimens
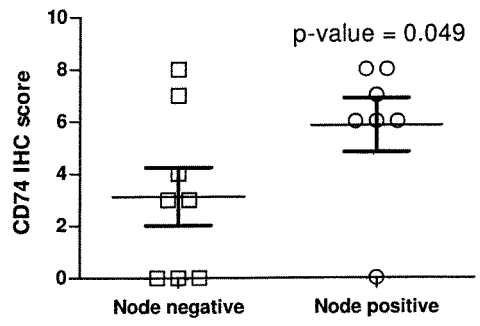
CD74 and Scribble spectral counts by LC-MS/MS
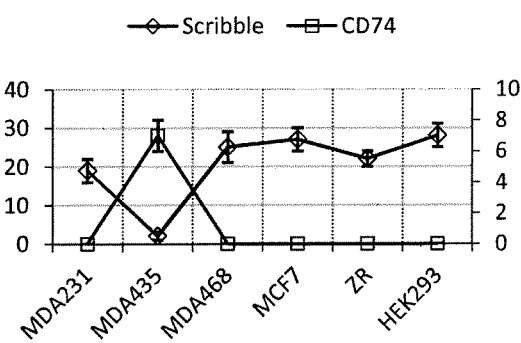

Figure 8A

```
>sp|Q14160|SCRIB_HUMAN Protein scribble homolog OS=Homo sapiens
GN=SCRIB PE=1 SV=4
MLKCIPLWRCNRHVESVDKRHCSLQAVPEEIYRYSRSLEELLLDANQLRELPKPFFRLLN
LRKLGLSDNEIQRLPPEVANFMQLVELDVSRNDIPEIPESIKFCKALEIADFSGNPLSRL
PDGFTQLRSLAHLALNDVSLQALPGDVGNLANLVTLELRENLLKSLPASLSFLVKLEQLD
LGGNDLEVLPDTLGALPNLRELWLDRNQLSALPPELGNLRRLVCLDVSENRLEELPAELG
GLVLLTDLLLSQNLLRRLPDGIGQLKQLSILKVDQNRLCEVTEAIGDCENLSELILTENL
LMALPRSLGKLTKLTNLNVDRNHLEALPPEIGGCVALSVLSLRDNRLAVLPPELAHTTEL
HVLDVAGNRLQSLPFALTHLNLKALWLAENQAQPMLRFQTEDDARTGEKVLTCYLLPQQP
PPSLEDAGQQGSLSETWSDAPPSRVSVIQFLEAPIGDEDAEEAAAEKRGLQRRATPHPSE
LKVMKRSIEGRRSEACPCQPDSGSPLPAEEEKRLSAESGLSEDSRPSASTVSEAEPEGPS
AEAQGGSQQEATTAGGEEDAEEDYQEPTVHFAEDALLPGDDREIEEGQPEAPWTLPGGRQ
RLIRKDTPHYKKHFKISKLPQEAVVALLQGMQPDGEGPVAPGGWHNGPHAPWAPRAQKE
EEEEEEGSPQEEEVEEEENRAEEEEASTEEDKEGAVVSAPSVKGVSFDQANNLLIEPA
RIEEEELTLTILRQTGGLGISIAGGKGSTPYKGDDEGIFISRVSEEGPAARAGVRVGDKL
LEVNGVALQGAEHHEAVEALRGAGTAVQMRVWRERMVEPENAVTITPLRPEDDYSPRERR
GGGLRLPLLPPESPGPLRQRHVACLARSERGLGFSIAGGKGSTPYRAGDAGIFVSRIAEG
GAAHRAGTLQVGDRVLSINGVDVTEARHDHAVSLLTAASPTIALLLEREAGGPLPPSPLP
HSSPPTAAVATTSITTATPGVPGLPSLAPSLLAAALEGPYPVEEIRLPRAGGPLGLSIVG
GSDHSSHPFGVQEPGVFISKVLPRGLAARSGLRVGDRILAVNGQDVRDATHQEAVSALLR
PCLELSLLVRRDPAPPGLRELCIQKAPGERLGISIRGGARGHAGNPRDPTDEGIFISKVS
PTGAAGRDGRLRVGLRLLEVNQQSLLGLTHGEAVQLLRSVGDTLTVLVCDGFEASTDAAL
EVSPGVIANPFAAGIGHRNSLESISSIDRELSPEGPGKEKELPGQTLHWGPEATEAAGRG
LQPLKLDYRALAAVPSAGSVQRVPSGAAGGK                         QA
YR                                   ERQKYFELEVRVPQAEGPPKRVSLV
GADDLRKMQEEEARKLQQKRAQMLREAAEAGAEARLALDGETLGEEEQEDEQPPWASPSP
TSR                   TAKAERRHQERLRVQSPEPPAPERALSPAELRALEAEKRAL
WRAARMKSLEQDALRAQMVLSRSQEGRGTRGPLERLAEAPSPAPTPSPTPVEDLGPQTST
SPGRLSPDFAEELRSLEPSPSPGPQEEDGEVALVLLGRPSPGAVGPEDVALCSSRRPVRP
GRRGLGPVPS
```

Detection of Scribble peptide QSPAS(ph)PPPIGGGAPVR by LC-MS/MS

DETECTION AND TREATMENT OF CANCER

FIELD OF THE INVENTION

The present invention relates to a prognostic biomarker and the use of the biomarker in methods for diagnosing, evaluating the prognosis and staging cancer in a patient. Also within the scope of the invention are kits and methods for the treatment of cancer.

BACKGROUND OF THE INVENTION

Worldwide, breast cancer is the second most common type of cancer and one of the most common causes of cancer death in humans. It is the most common cancer in women. Breast cancer is a heterogeneous disease that is treated by surgery, chemotherapy and several rationale-based targeted therapies. The choice of optimal course of treatment depends on the availability of biomarkers, which are measured by appropriate clinical assays. Unfortunately, at the present very few useful biomarkers have been identified and translated to clinical use. These are the oestrogen receptor (ER), progesterone receptor (PR) and the ErbB2 receptor. These three markers are very useful but about a third of diagnosed cases are triple-negative. In other words, the tumours do not express ER, PgR and Her2. For this type of breast cancer new biomarkers and diagnostic and prognostic assays are in high demand.

Cancer metastasis is a multistage process that is governed by a complex program of gene expression and signal transduction that ultimately allows the metastasizing cells to invade surrounding stroma, travel through the circulation, and colonize distant sites. This program sequentially switches specific genes on and turns others off, effectively exerting very dramatic changes of the abundance of many hundreds of proteins in the cell. Since the completion of the human genome project, post-genomic approaches based on application of oligonucleotide microarrays and next-generation sequencing are beginning to shed light on the global cancer genomics landscape and its molecular landmarks.

In addition, developments in quantitative proteomics now allow us to dig even deeper: to map the posttranslational modifications and protein-protein interactions that are at the core of the regulation of the molecular mechanisms that drive metastasis. Here I describe one such quantitative proteomics approach to investigate the role of CD74 in promoting metastasis of triple-negative breast cancer, a particularly malignant type of the disease.

CD74, the γ subunit of the major histocompatibility complex (MHC) class II complex, is frequently overexpressed in malignant tumors of epithelial and mesenchymal origin. The protein has been suggested as a potential target for rationale-based therapies of lymphoma and multiple myeloma and therapeutic agents targeting CD74 or components of its signaling cascade are in advanced stages of clinical development [1-3]. More recently, I and others reported that CD74 overexpression is linked to increased invasion and metastasis of breast tumors, particularly the tumors of the triple-negative phenotype [4,5]. CD74 is a chaperone protein with an important role in innate immunity. It is required for the expression and functions of the MHC class II receptors and, in addition, has been implicated in cytokine and survival signaling [6-8]. However, the mechanistic foundation for the apparent CD74-augmented malignancy of triple-negative breast tumors is not known. To address this, I have engineered human epithelial cells to express CD74 under the control of a highly regulated inducible promoter, which allowed us to study the effect of CD74 overexpression on protein abundance and protein phosphorylation at a system-wide scale.

I have surprisingly identified that when overexpressed, CD74 affects the phosphorylation state and function of Scribble, a product of the well-known tumor suppressor gene scrib, which is crucial for the proper maintenance of epithelial cell integrity and function and which is frequently deregulated in breast cancer [9]. Scribble function in maintaining polarity was first discovered in *Drosophila*. Bilder et al. found that scrib mutations cause aberrant cell shape and loss of monolayer organization in epithelia [10] and that scrib acts as a tumor suppressor [11]. In human cells, Scribble is required for E-cadherin-mediated cell-cell adhesion, and when its expression is downregulated, epithelial cells acquire mesenchymal appearance and their migration is augmented [12].

The invention is aimed at providing methods for the detection and prognosis of cancer, in particular epithelial cancer.

SUMMARY OF THE INVENTION

In the present invention I describe a new prognostic biomarker: Scribble. Accordingly, a first aspect of the present invention provides a method of diagnosing cancer in a patient, the method comprising detecting the phosphorylation status of a Scribble protein, a fragment or variant thereof, wherein said phosphorylation status is indicative of cancer.

In a second aspect of the invention I provide a method of detecting cancer metastasis in a patient, the method comprising detecting the phosphorylation status of a Scribble protein, a fragment or variant thereof, wherein the phosphorylation status is indicative of metastasis.

In a third aspect of the invention I provide a method for evaluating the prognosis of cancer, the method comprising detecting the phosphorylation status of a Scribble protein, a fragment or variant thereof, wherein the phosphorylation status is indicative of prognosis. Thus, the present method permits the differentiation of cancer patients with a good prognosis (i.e. disease-free survival) from those patients with a bad prognosis.

In a fourth aspect of the invention I provide a method of selecting a treatment for cancer, the method comprising detecting the phosphorylation status of a Scribble protein, a fragment or variant thereof and selecting a treatment depending on said phosphorylation status.

In a fifth aspect of the invention I provide a method of selecting a subject for the treatment of cancer, the method comprising detecting the phosphorylation status of a Scribble protein, a fragment or variant thereof and selecting a subject depending on said phosphorylation status.

In a further aspect of the invention I provide a method for detecting the phosphorylation status of a Scribble protein with SEQ ID NO: 1, a fragment or variant thereof, the method comprising:
obtaining a sample from a patient and contacting the sample with at least one antibody that is capable of specifically binding phosphorylated or unphosphorylated residues S1306, S1309, S1348 and S1448 or a combination thereof in the Scribble protein, fragment or variant thereof. In one embodiment, the method is performed in conjunction with at least one of the following: evaluating cancer prognosis, developing a cancer treatment plan, assessing the efficiency of cancer treatment and the likelihood of metastases.

In a further aspect of the invention I provide a method for monitoring the effectiveness of a treatment, the method comprising detecting the phosphorylation status of a Scribble protein, a fragment or variant thereof, and determining effectiveness of a treatment.

The present invention also contemplates the assessment of the phosphorylation status of the Scribble protein, a fragment or variant thereof, where the phosphorylation status indicates an increased aggressiveness (e.g. metastatic potential) of the cancer tumor. As such, the phosphorylation status of the Scribble protein serves as a predictor of disease status and stage. The invention therefore relates to methods for assessing the aggressiveness of a tumor comprising assessing the phosphorylation status of the Scribble protein, a fragment or variant thereof.

In another aspect, the invention provides a method for monitoring disease progression comprising assessing the phosphorylation status of the Scribble protein, a fragment or variant thereof. For example, changes in the patient's condition can be monitored by comparing changes in the phosphorylation status of the Scribble protein, a fragment or variant thereof in the patient over time. Progressive decreases in the phosphorylation status of the Scribble protein, a fragment or variant thereof are indicative of increased potential for tumor invasion and metastasis.

In one embodiment of any of the above methods described herein, the method comprises detecting the phosphorylation status of one or more residues of a Scribble protein, fragment or variant thereof. In a preferred embodiment, the method comprises detecting the phosphorylation status of at least one of the following residues S1306, S1309, S1348 and S1448 or a combination thereof. In a further preferred embodiment the method comprises detecting the phosphorylation of no other residues than S1306, S1309, S1348 and S1448.

In one embodiment of the methods described herein, the cancer is epithelial cancer. In a preferred embodiment, the cancer is breast, pancreas, bone, liver, stomach, lung (for example non-small cell lung cancer (NSCLC)), colorectal, bladder, prostate, head and neck cancer or ovarian cancer. In a more preferred embodiment, the cancer is breast cancer and the breast cancer tumour does not express at least one marker selected from the group consisting of oestrogen receptor (ER), progesterone receptor (PgR) and the ErbB2 receptor. This is known as triple negative breast cancer.

In a further embodiment of the methods described herein, detecting the phosphorylation status comprises obtaining a sample from said patient and contacting the sample with at least one antibody that is capable of specifically binding phosphorylated residues of a Scribble protein, fragment or variant thereof. In an alternative embodiment, detecting the phosphorylation status comprises obtaining a sample from said patient and detecting the phosphorylation status by mass spectrometry. In a further embodiment, the method comprises detecting the expression of one or more other biomarkers. In a further embodiment this can comprise detecting the expression levels of the Scribble protein, or a fragment or variant thereof. The methods further comprise comparing the phosphorylation status of Scribble in the patient's test sample with the phosphorylation status of Scribble in a control or reference sample.

In one embodiment of the methods described herein, the patient has or is at risk of developing cancer. In an alternative embodiment the patient has no clinical signs or manifestations of cancer (i.e. the patient is asymptomatic). In a preferred embodiment, the patient is a human patient.

In an additional embodiment of the methods described herein, the method comprises detecting the phosphorylation status, and preferably measuring the concentration of at least one of the phosphorylated peptides from Table 1, preferably using mass spectrometry or antibodies. In a preferred embodiment the phosphopeptides are measured by mass spectrometry using internal standards having the same amino acid sequence and posttranslational modifications but labelled with stable isotopes.

In one embodiment, the subject invention does not comprise the step of determining Scribble expression level in the subject's sample.

In a further aspect of the invention there is provided a kit. In a preferred embodiment the kit is suitable for implementing any of the above described methods. In one embodiment the kit comprises at least one antibody, wherein the or each of said antibody is capable of binding to at least one phosphorylated or unphosphorylated residue in a Scribble protein, or fragment or variant thereof, selected from S1306, S1309, S1348 and S1448 or a combination thereof. In a preferred embodiment the kit comprises agents for the detection of the at least one antibody binding to said phosphorylated residues in Scribble. In a further embodiment the kit comprises instructions for use. In a further embodiment the kit comprises a positive control sample.

In a further aspect of the invention there is provided an antibody capable of selectively binding to at least one phosphorylated residue in a Scribble protein, or fragment or variant thereof, wherein said residue is selected from S1306, S1309, S1348 and S1448 or a combination thereof. In an alternative aspect of the invention there is provided an antibody capable of selectively binding to at least one unphosphorylated residue in a Scribble protein, or fragment or variant thereof, wherein said residue is selected from S1306, S1309, S1348 and S1448 or a combination thereof.

In a another aspect of the invention there is provided a method of treating cancer, the method comprising administering an agent capable of phosphorylating or preventing the dephosphorylation of a Scribble protein, or fragment or variant thereof. In one embodiment, the agent is capable of phosphorylating or preventing the dephosphorylation of at least one residue in a Scribble protein, fragment or variant thereof, wherein said residue is selected from S1306, S1309, S1348 and S1448 or a combination thereof.

In a final aspect of the invention there is provided a pharmaceutical composition comprising an agent capable of phosphorylating or preventing the dephosphorylation of at least one residue in a Scribble protein, fragment or variant thereof, wherein said residue is selected from S1306, S1309, S1348 and S1448 or a combination thereof, and a pharmaceutically acceptable carrier.

DESCRIPTION OF THE FIGURES

The invention is further described in the following non-limiting figures.

FIG. 1 shows the effect of CD74 overexpression on the pattern of posttranslational modifications of the tumour suppressor protein Scribble.

CD74 overexpression affects the pattern of posttranslational modifications of the tumor suppressor protein Scribble. (A) Domain map of Scribble based on a cartoon from the SMART database showing the four phosphorylation hotspots in the C-terminal part of the protein affected by CD74 overexpression in HEK293 and MCF7 cells. The three sites were identified in quantitative proteomics/phosphoproteomics screens using transiently transfected MCF7 and HEK293 cells and stably transfected HEK293s cells expressing CD74 under the control of tetracycline-inducible promoter. (B) Scatterplot of Scribble phosphopeptides detected by high-resolution LC-MS/MS analysis. The normalized heavy-to-light ratios are plotted against the *Andromeda* score. Two clusters of data points are apparent: a set of phosphopeptides that center around H/L ratio of 1, which are not affected by CD74 overexpress ion, and another cluster that contains the phosphopeptides that are strongly decreased in the CD74-overexpressing cells. The P value was calculated by the Student's t test using the normalized H/L ratios of the two clusters indicated by grey borders. (C) Zoom-in of the isotope envelops of two phosphopeptide ions showing large difference between the intensities of the light peptide ions and the heavy counterparts deriving from CD74-overexpressing cells. The phosphopeptide sequences are indicated under the spectra.

Figure 2:
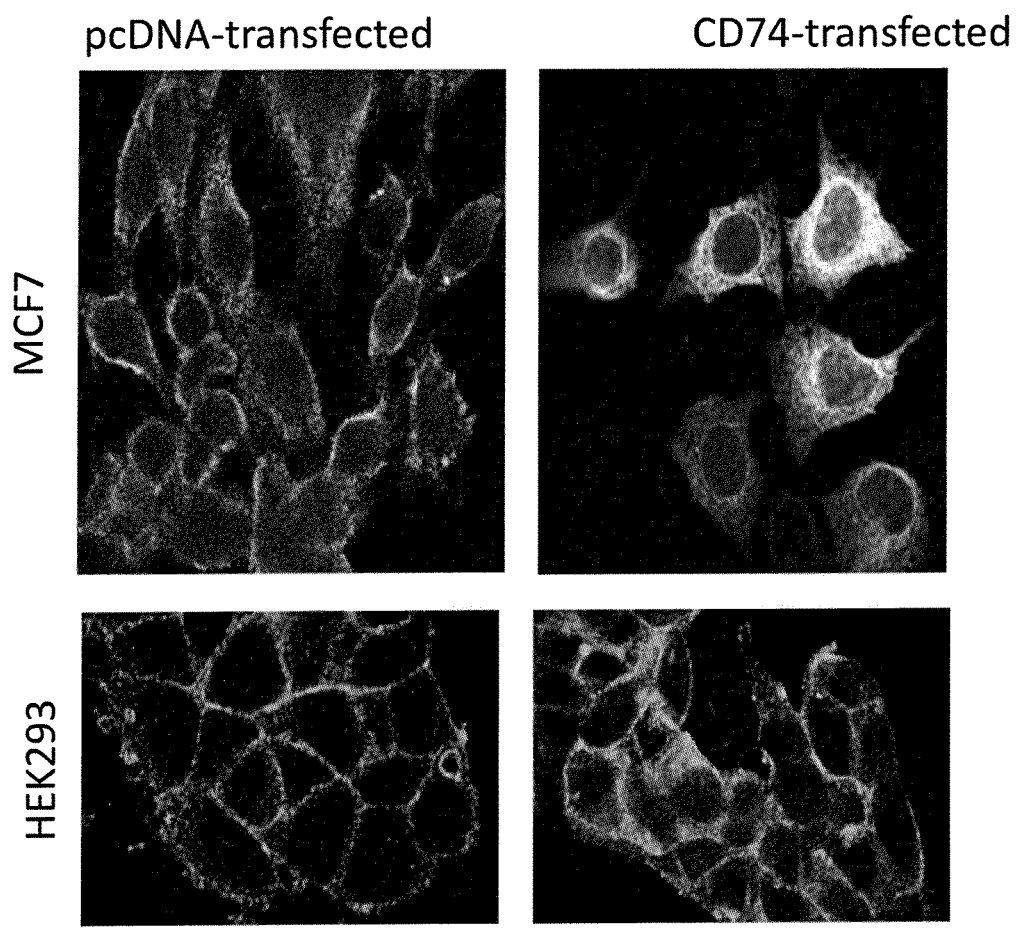

FIG. 2 shows Scribble mislocalisation in CD74-overexpressing cells. Laser scanning confocal images of control and transfected MCF7 and HEK293 cells stained with mouse monoclonal anti-Scribble primary antibodies and anti-mouse fluorescein isothiocyanate conjugate. Representative focal planes taken from the midsection of the cells are shown.

FIG. 3 shows Scribble expression in stably transfected HEK293s cells expressing CD74 under the control of tetracycline-inducible promoter.

(A) Western blot analysis showing the same Scribble abundance in the fully denatured and unfolded samples extracted from control and tetracycline-induced cells. (B) The same cell cultures as in A show increased Scribble staining in the CD74-overexpressing cells in FACS assays despite the fact that the same anti-Scribble primary antibody is used. The filled-in gray histogram is from secondary antibody-only control. (C) The same cell cultures as in A and B show increased Scribble staining by confocal microscopy. The same primary antibody is used.

Figure 4:
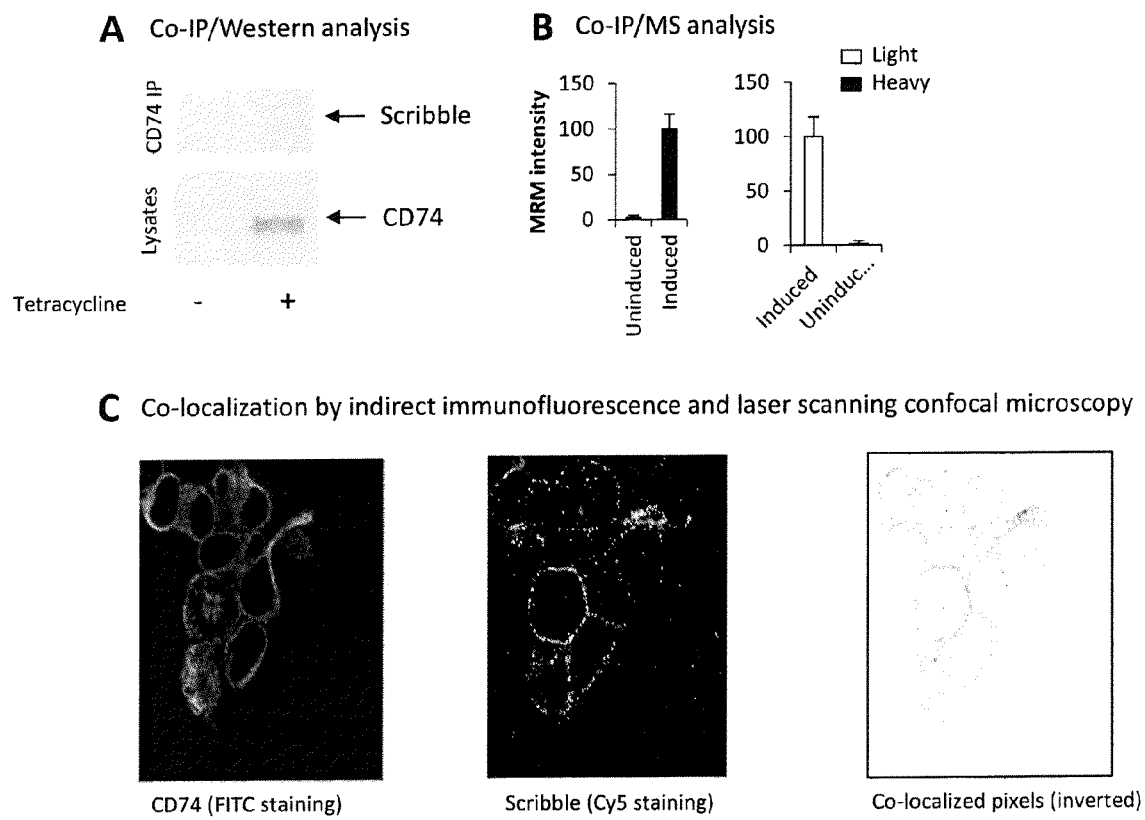

FIG. 4 shows Scribble and CD74 copurified from membrane protein isolates and colocalize in stably transfected HEK293s cells. (A) Co-IP/Western blot analysis. Scribble is detected only in the CD74 IP from cells induced with tetracycline to express CD74. (B) Co-IP/MS. The multiple reaction monitoring (MRM) signal for the reporter peptides is normalized to 100. The values are mean of three replicate LC-MS/MS analyses±SD. This experiment was performed twice. First, CD74 expression was induced in the heavy SILAC-labeled cells. Then, the protein was overexpressed in the light SILAC-labeled cells. In both experiments, MaxQuant detected Scribble peptides only in the CD74 IP from tetracycline-induced cells. (C) Colocalization of Scribble and CD74 in HEK293s cells overexpressing CD74.

Figure 5:
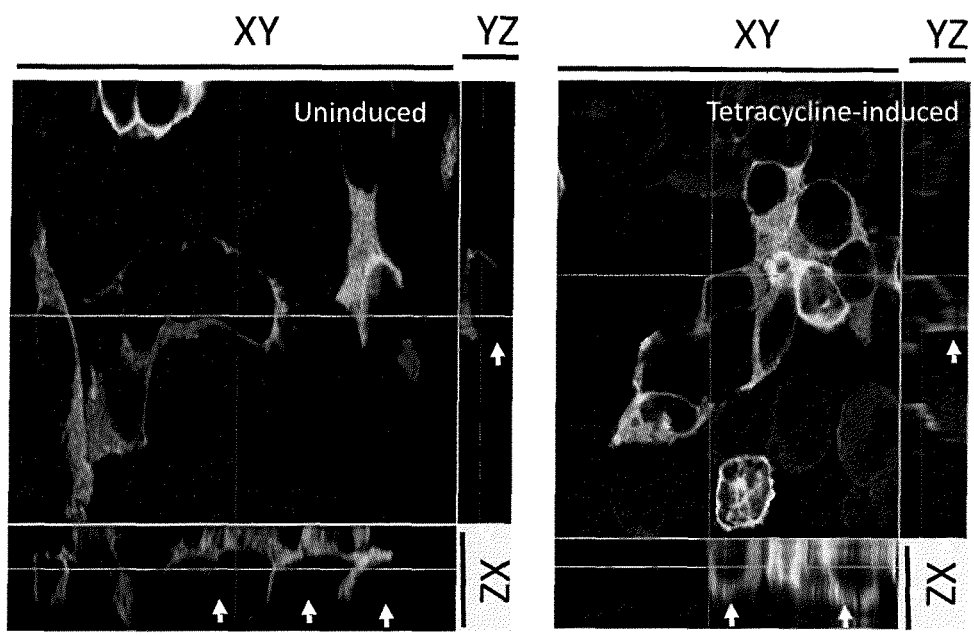

FIG. 5 shows that overexpression of CD74 induces translocation of a subpopulation of Scribble molecules from the basolateral side to the apical side of the cells. GFP-Scribble was transiently transfected in TetO-CD74 HEK293s cells and the expression of CD74 was induced with tetracycline. After 24 hours of induction, the cells were fixed and stained with anti-CD74 antibody and analyzed by laser scanning confocal microscopy. The image is presented as "Slice View," in which the three orthogonal planes XY (the midsection of the stack), YZ, and XZ are formed by slicing the stack as indicated by the crossed orange lines. The white arrows point to the apical side of the cells where GFP-Scribble can be seen only in the cells overexpressing CD74.

FIG. 6 shows Overexpression of CD74 in lymph node-metastatic triple-negative breast tumors. (Top) Formaldehyde-fixed section from a tumor was stained with secondary antibody only (A); CD74 staining in a section from node-negative tumor showing positive staining in infiltrating lymphocytes and negative malignant cells (B); CD74 staining in a node-positive triple-negative tumor showing strong cytoplasmic staining of the malignant cells (C). (Bottom left) CD74 IHC scores for node-positive (n=9) and node-negative (n=10) tumors. The mean and SEM are indicated by horizontal lines. The P value of 0.0409 was calculated by one-tailed nonparametric Mann-Whitney t test. A one-tailed Fisher's exact test assuming cut value of 5 returns a P value of 0.051. (Bottom right) CD74 and Scribble abundances in the membrane fractions of cultured breast cancer cell lines and the HEK293s cell line. The abundance was estimated by the spectral count method in triplicate LC-MS/MS analyses. CD74 spectral counts are plotted on the right y-axis. The protein was only detected in MDA-435-MB. Scribble spectral counts are plotted on left y-axis. Vertical bars represent SDs. Only MS/MS spectra passing the 1% FDR threshold as calculated by MaxQuant were included in the analysis. Scribble is barely detectable with one to two spectral counts in MDA-435-MB.

Figure 7:
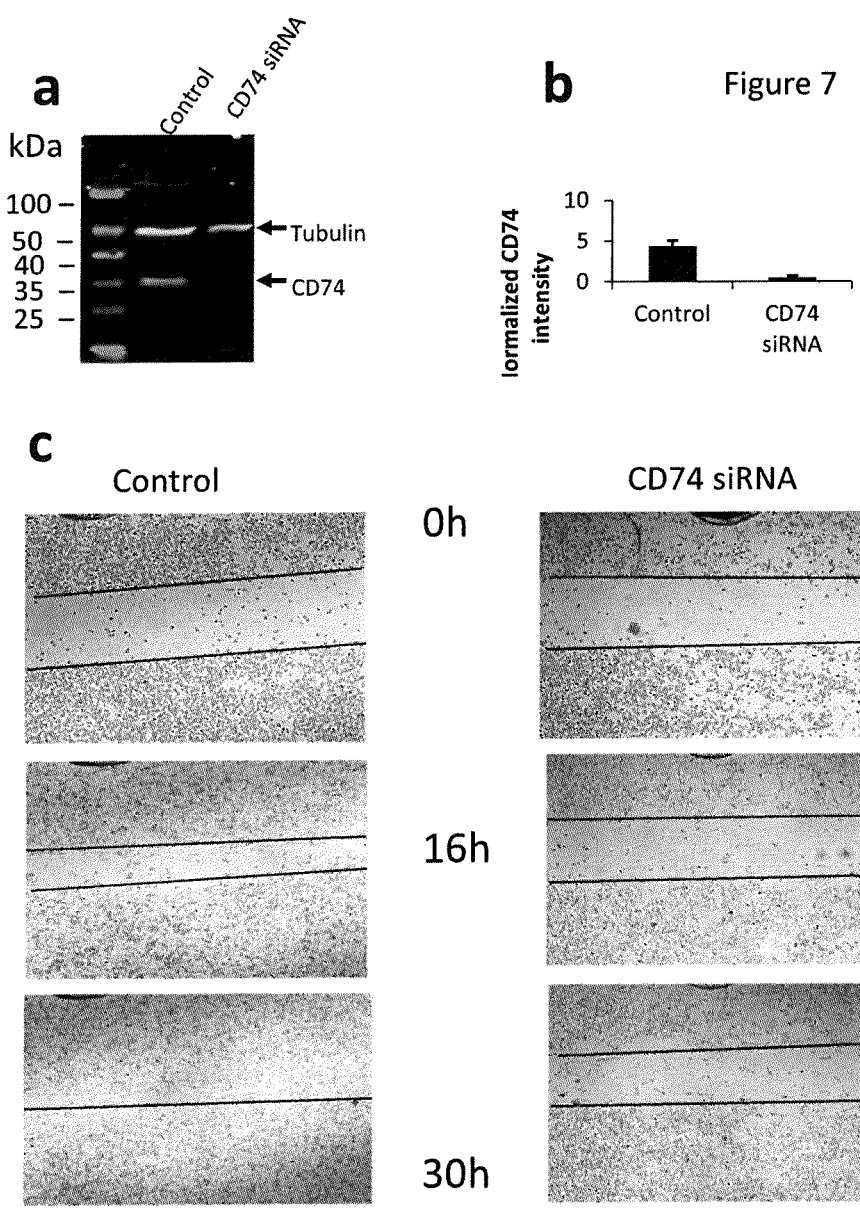

FIG. 7 shows CD74 knockdown affects the wound healing in MDA-435-MB. (A) Western blot analysis of CD74 abundance in cells transfected with control DNA (left) and CD74 siRNA performed 18 hours after transfection. (B) Bar graph is based on two replicate analyses. (C) Wound healing assay with control and CD74 siRNA-transfected cells. The assays were started 18 hours after transfection. Photographs were taken at 0, 16, and 30 hours.

Figure 8:
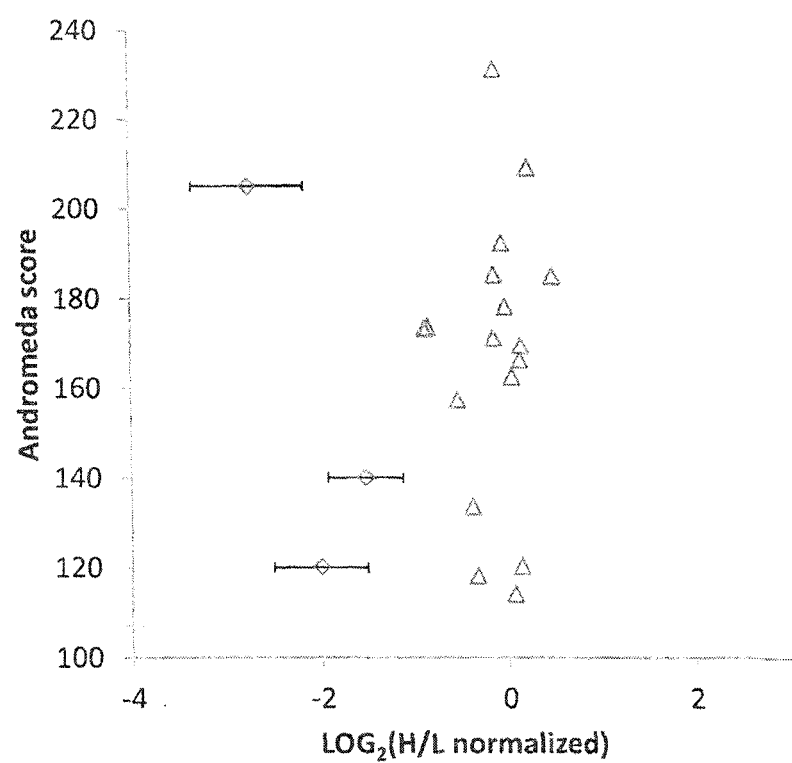

FIG. 8 shows (8A) Scribble peptides and phosphorylation sites detected in immunoprecipitated Scribble by high-resolution mass spectrometry. The detected peptides are shown as boxed sequences highlighted in yellow. The three phosphopeptides affected by CD74 overexpression are highlighted in blue with phosphoserines shown in red. (8B) Measured H/L ratios for the high-scoring Scribble peptides (*Andromeda* score>100) showing that the unmodified peptides center on a normalized H/L ratio of 1 (blue symbols). The three phosphorylated peptides, shown with red symbols±SD, are significantly decreased in the heavy Scribble molecules coming from CD74-overexpressing cells. For each of the phosphopeptides, the Student's two-tailed t test returns a P value that is lower than 0.0001 when calculated against the normalized H/L ratios of the unmodified peptides shown with blue triangles.

Figure 9:
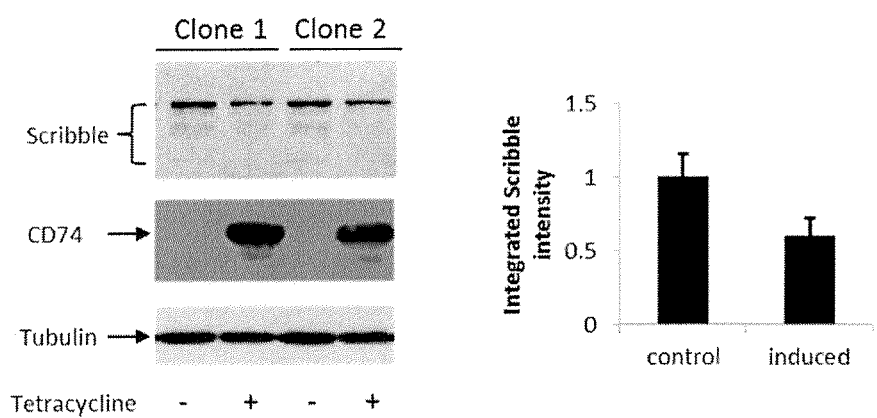

FIG. 9 shows that long-term overexpression of CD74 leads to a decrease of Scribble abundance as determined by Western blot analysis. (Left) Scribble detection in lysates from uninduced TetR/TetO-CD74 cells and cells induced with tetracycline for 48 hours. (Right) Bar graph of the integrated band intensities of Scribble determined by the infrared fluorescent scanner in two independent experiments. The intensities were normalized against tubulin.

Figure 10:
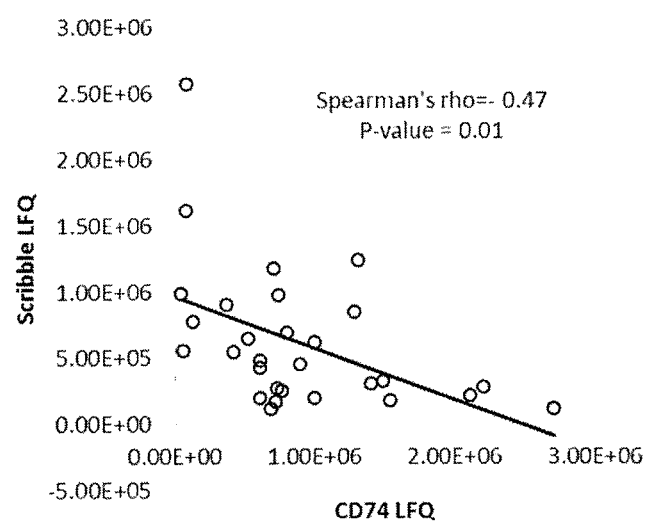

FIG. 10 shows label-free quantitation (LFQ) of CD74 and Scribble in membrane isolates of 25 breast tumor biopsies. The membrane proteins were isolated by the permeabilization and extraction procedure, digested with trypsin, and analyzed by LC-MS/MS as described in Materials and Methods section. MaxQuant was used to process the LC-MS/MS data and calculate LFQ as described in [28]. The nonparametric Spearman $\rho$ and corresponding P values were calculated in R using cor.test.

Figure 11:
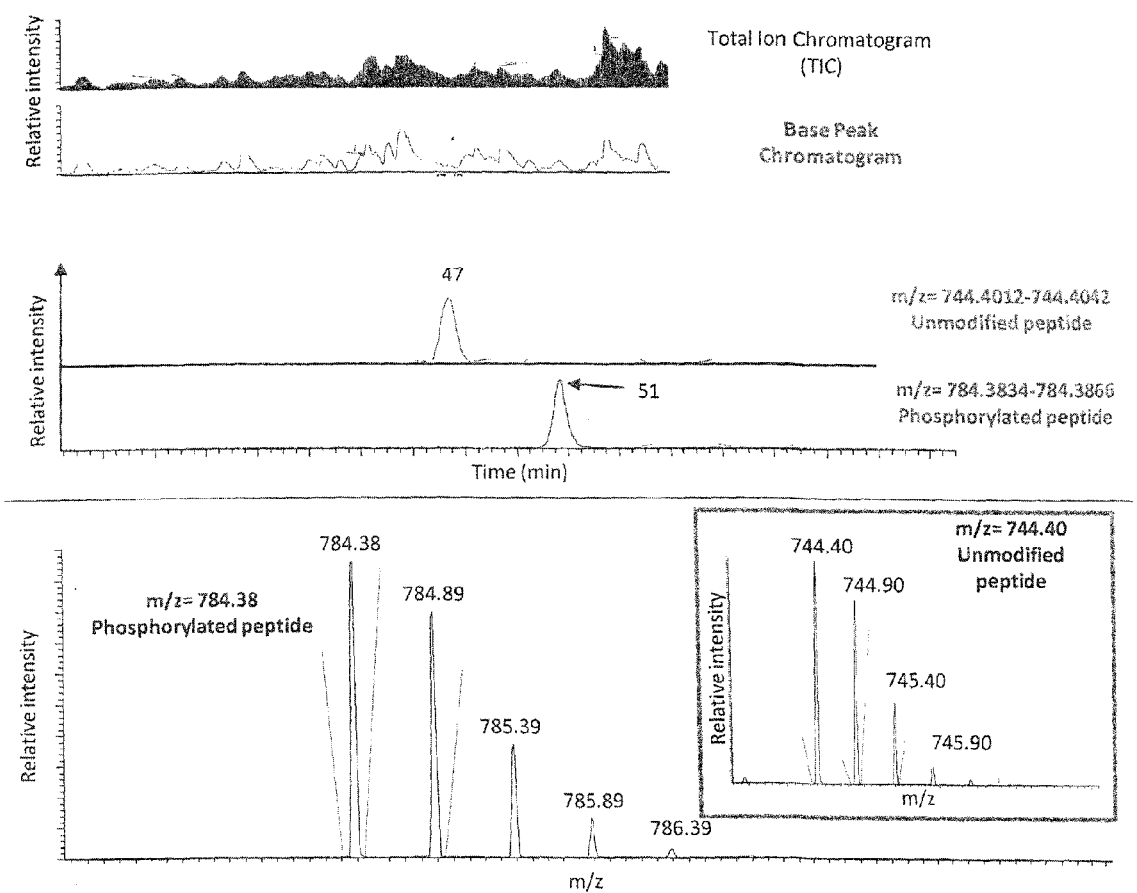

FIG. 11 shows the detection of phosphorylated peptide QSPAS(ph)PPPLGGGAPVR (SEQ ID NO: 15) derived from human Scribble expressed in HEK293 cells as a GFP-tagged recombinant protein. Scribble was immunoprecipitated using a monoclonal anti-GFP antibody, digested with trypsin and analyzed by nano-scale LC-MS/MS. The phosphorylation sites was mapped to the serine residue at position 5 and is indicated with (ph) after the acceptor residue. The top trace is total ion chromatogram (TIC). Below is the base peak chromatogram trace in red. The phosphorylated peptide is detected as doubly-charged ion with a mass to charge ratio of 784.385. The extracted ion chromatogram for this eptide is shown as a blue trace. The isotopic cluster of this peptide ion is shown in the zoomed in high-resolution spectrum on the bottom. The unphosphorylated peptide was also detected as a doubly-charged ion with m/z of 744.402. Its extracted ion chromatogram is shown with a green trace and spectrum in the insert framed in blue.

DETAILED DESCRIPTION OF THE INVENTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features being indicated as being preferred or advantageous.

The inventor has surprisingly shown that when overexpressed, CD74 affects the phosphorylation state, localisation and hence function of Scribble, a product of the well-known tumor suppressor gene SCRIB. SCRIB is crucial for the proper maintenance of epithelial cell integrity and function and is frequently deregulated in breast cancer. Furthermore, using epithelial cell lines expressing CD74 under the control of tetracycline-inducible promoter and quantitative high-resolution mass spectrometry, I demonstrate that, as a result of CD74 overexpression, the phosphorylation pattern of the C-terminal part of Scribble undergoes specific changes. This is accompanied with a translocation of the protein from the sites of cell-to-cell contacts at the plasma membrane to the cytoplasm, which is likely to effectively enhance the motility and invasiveness of the cancer cells. Accordingly, the inventor describes a new prognostic biomarker, Scribble.

The term 'Scribble protein' refers to the protein encoded by SCRIB (scribbled planar cell polarity protein) and represented by SEQ ID NO: 1.

```
SEQ ID NO: 1:
   1    mlkciplwrc nrhvesvdkr hcslqavpee iyrysrslee llldanqlre
        lpkpffrlln 61    lrklglsdne iqrlppevan fmqlveldvs rndipeipes ikfckaleia
        dfsgnplsrl 121    pdgftqlrsl ahlalndvsl qalpgdvgnl anlvtlelre nllkslpasl
        sflvkleqld 181    lggndlevlp dtlgalpnlr elwldrnqls alppelgnlr rlveldvsen
        rleelpaelg 241    glvlltdlll sqnllrrlpd gigqlkqlsi lkvdqnrlce vteaigdcen
        lseliltenl 301    lmalprslgk ltkltnlnvd rnhlealppe iggcvalsvl slrdnrlavl
        ppelahttel 361    hvldvagnrl qslpfalthl nlkalwlaen qaqpmlrfqt eddartgekv
        ltcyllpqqp 421    plsledagqq gslsetwsda ppsrvsviqf leapigdeda eeaaaekrgl
        qrratphpse 481    lkvmkrsieg rrseacpcqp dsgsplpaee ekrlsaesgl sedsrpsast
        vseaepegps 541    aeaqggsqqe attaggeeda eedyqeptvh faedallpgd dreieegqpe
        apwtlpggrq 601    rlirkdtphy kkhfkisklp qpeavvallq gmqpdgegpv apggwhngph
        apwapraqke 661    eeeeegspq eeeeeeeen raeeeeaste eedkegavvs apsvkgvsfd
        qannlliepa 721    rieeeeltlt ilrqtgglgi siaggkgstp ykgddegifi srvseegpaa
        ragvrvgdkl 781    levngvalqg aehheaveal rgagtavqmr vwrermvepe navtitplrp
        eddysprerr 841    ggglrlpllp pespgplrqr hvaclarser glgfsiaggk gstpyragda
        gifvsriaeg 901    gaahragtlq vgdrvlsing vdvtearhdh ayslltaasp tialllerea
        ggplppsplp 961    hsspptaava ttsittatpg vpglpslaps llaaalegpy pveeirlpra
        ggplglsivg 1021    gsdhsshpfg vqepgvfisk vlprglaars glrvgdrila vngqdvrdat
        hqeaysallr 1081    pclelsllvr rdpappglre lciqkapger lgisirggar ghagnprdpt
        degifiskvs
```

```
-continued 1141    ptgaagrdgr lrvglrllev nqqsllglth geavqllrsv gdtltvlvcd
        gfeastdaal 1201    evspgvianp faagighrns lesissidre lspegpgkek elpgqtlhwg
        peateaagrg 1261    lqplkldyra laavpsagsv qrvpsgaagg kmaespcsps gqqppsppsp
        delpanvkqa 1321    yrafaavpts hppedapaqp ptpgpaaspe qlsfrerqky felevrvpqa
        egppkrvslv 1381    gaddlrkmqe eearklqqkr aqmlreaaea gaearlaldg etlgeeeqed
        eqppwaspsp 1441    tsrqspaspp plgggapvrt akaerrhqer lrvqspeppa peralspakl
        raleaekral 1501    wraarmksle qdalraqmvl srsqegrgtr gplerlaeap spaptpsptp
        vedlgpqtst 1561    spgrlspdfa eelrslepsp spgpqeedge valvllgrps pgavgpedva
        lcssrrpvrp 1621    grrglgpvps
```

The nucleic acid sequence encoding Scribble (NG 030583.1) is incorporated herein by reference.

The term 'a Scribble protein' also encompasses all alternatively spliced isoforms. The term also encompasses all fragments and variants thereof.

The term 'fragment' refers to a portion of the amino acid sequence that is less than the complete length and includes at least a minimum length capable of maintaining the biological properties required in the present invention. In a preferred embodiment the fragment is between residues 1295 and 1448 inclusive. In a further preferred embodiment the fragment is between residues 1306 and 1448 inclusive. In a further preferred embodiment the fragment is between 13006 and 1348 inclusive.

The term 'variant' refers to the protein sequence where the amino acids are substantially identical to SEQ ID NO: 1. A variant retains the biological function and activity of the Scribble protein. The variant may be achieved by modifications such as insertion, substitution or deletion of one or more of the amino acids. In a preferred embodiment, the variant thereof has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to SEQ ID NO:1.

A cancer is an example of a proliferative disorder. Cells characteristic of proliferative disorders (i.e., "neoplastic cells" or "tumor cells") have the capacity for autonomous growth, i.e., an abnormal state or condition characterized by inappropriate proliferative growth of cell populations. A neoplastic cell or a tumor cell is a cell that proliferates at an abnormally high rate. A new growth comprising neoplastic cells is a neoplasm, also known as a "tumor." A tumor is an abnormal tissue growth, generally forming a distinct mass that grows by cellular proliferation more rapidly than normal tissue. A tumor may show a partial or total lack of structural organization and functional coordination with normal tissue. As used herein, a tumor is intended to encompass hematopoietic tumors as well as solid tumors.

A tumor may be benign (benign tumor) or malignant (malignant tumor or cancer). Malignant tumors can be broadly classified into three major types. Malignant tumors arising from epithelial structures are called carcinomas; malignant tumors that originate from connective tissues such as muscle, cartilage, fat, or bone are called sarcomas; and malignant tumors affecting hematopoietic structures (structures pertaining to the formation of blood cells) including components of the immune system are called leukemias and lymphomas, Ewing's sarcomas, osteosarcomas, and chondrosarcomas.

The methods described herein are particularly relevant for the treatment of humans having an epithelial malignancy. Epithelial malignancies are cancers that affect epithelial tissues, such as a lung cancer (e.g., non-small-cell lung cancer (NSCLC)), breast cancer, colorectal cancer, head and neck cancer, prostate or ovarian cancer. In a preferred embodiment, the cancer is breast cancer.

The term 'breast cancer' refers to those conditions classified by biopsy as malignant pathology. The clinical delineation of breast cancer diagnoses is well-known in the medical arts. One of skill in the art will appreciate that breast cancer refers to any malignancy of the breast tissue, including, for example, carcinomas and sarcomas. In particular embodiments, the breast cancer is ductal carcinoma in situ (DCIS), lobular carcinoma in situ (LCIS), or mucinous carcinoma. Breast cancer also refers to infiltrating ductal (IDC) or infiltrating lobular carcinoma (ILC). In most embodiments of the invention, the subject of interest is a human patient suspected of or actually diagnosed with breast cancer.

The term 'staging' refers to the stage of cancer, and can be defined in one example by reference to the American Joint Committee on Cancer (AJCC), which has developed a standardized system for breast cancer staging using a "TNM" classification scheme. Patients are assessed for primary tumour size (T), regional lymph node status (N), and the presence/absence of distant metastasis (M) and then classified into stages 0-IV based on this combination of factors. In this system, primary tumour size is categorized on a scale of 0-4 (T0=no evidence of primary tumour; T1=<=2 cm; T2=>2 cm-<5 cm; T3=>5 cm; T4=tumour of any size with direct spread to chest wall or skin). Lymph node status is classified as N0-N3 (N0=regional lymph nodes are free of metastasis; N1=metastasis to movable, same-side axillary lymph node(s); N2=metastasis to same-side lymph node(s) fixed to one another or to other structures; N3=metastasis to same-side lymph nodes beneath the breastbone). Metastasis is categorized by the absence (M0) or presence of distant metastases (M1).

Methods of identifying breast cancer patients and staging the disease are well known and may include manual examination, biopsy, review of patient's and/or family history, and imaging techniques, such as mammography, magnetic resonance imaging (MRI), and positron emission tomography (PET).

A "subject" as described herein can be any subject having a proliferative disorder. For example, the subject can be any mammal, such as a human, including a human cancer patient. Exemplary nonhuman mammals include a nonhuman primate (such as a monkey or ape) and a rodent, such as mouse or rat.

Accordingly, the invention relates to method of diagnosing cancer in a patient, the method comprising detecting the phosphorylation status of a Scribble protein, a fragment or variant thereof, wherein said phosphorylation status is indicative of cancer. In a preferred embodiment the method comprises detecting the phosphorylation status of one or more residues of a Scribble protein or fragment or variant thereof.

In another aspect the invention relates to a method of detecting cancer metastasis in a patient, the method comprising detecting the phosphorylation status of a Scribble protein, a fragment or variant thereof, wherein the phosphorylation status is indicative of metastasis.

The term 'metastasis' refers to a complex series of steps in which neoplasic cells leave the original tumor site and migrate to other parts of the body via the blood stream or the lymphatic system and start new tumors that resemble the primary tumor. Breast cancer cells are often transported through the lymphatic pathway to bone or other areas such as liver, lung or brain. It may be crucial to the survival of the patient to predict whether a primary cancer has the potential to metastasize such that high risk patients can be subject to closer follow up or specific treatment regime that will vary where the cancer has metastasized. Currently there is no way to visualize metastatic tumors so that effectiveness of therapy can be more easily monitored. Currently, detection of metastatic sites requires numerous, time consuming and costly tests that does not have very high specificity.

In a further aspect, the invention relates to a method for evaluating the prognosis of a cancer the method comprising detecting the phosphorylation status of a Scribble protein, a fragment or variant thereof, wherein the phosphorylation status is indicative of prognosis. In other words, the phosphorylation status is indicative or a good or poor prognosis. Following evaluating the prognosis, a proper course of treatment for a patient/subject having cancer may be determined. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

The term 'prognosis' refers to predictions about the likely course of disease or disease progression, particularly with respect to likelihood of disease remission, disease relapse, tumor recurrence, metastasis, and death. "Good prognosis" refers to the likelihood that a patient afflicted with cancer, particularly breast cancer, will remain disease-free (i.e., cancer-free). "Poor prognosis" is intended to mean the likelihood of a relapse or recurrence of the underlying cancer or tumor, metastasis, or death. Cancer patients classified as having a "good outcome" remain free of the underlying cancer or tumor. In contrast, "bad outcome" cancer patients experience disease relapse, tumor recurrence, metastasis, or death. In particular embodiments, the time frame for assessing prognosis and outcome is, for example, less than one year, one, two, three, four, five, six, seven, eight, nine, ten, fifteen, twenty or more years. As used herein, the relevant time for assessing prognosis or disease-free survival time begins with the surgical removal of the tumor or suppression, mitigation, or inhibition of tumor growth. Thus, for example, in particular embodiments, a "good prognosis" refers to the likelihood that a cancer, for example breast cancer patient, will remain free of the underlying cancer or tumor for a period of at least five, more particularly, a period of at least ten years. In further aspects of the invention, a "bad prognosis" refers to the likelihood that a cancer, for example breast cancer patient, will experience disease relapse, tumor recurrence, metastasis, or death within less than five years, more particularly less than ten years. Time frames for assessing prognosis and outcome provided above are illustrative and are not intended to be limiting.

In a further aspect, the invention relates to a method of selecting a treatment for the treatment of cancer, the method comprising detecting the phosphorylation status of a Scribble protein, a fragment or variant thereof and selecting a treatment depending on said phosphorylation status. In an alternative aspect, the invention relates to a method of selecting a subject for the treatment of cancer, the method comprising detecting the phosphorylation status of a Scribble protein, a fragment or variant thereof and selecting a subject depending on said phosphorylation status.

'Treatment' refers to the management of a patient through medical or surgical means. The treatment improves or alleviates at least one symptom of a medical condition or disease and is not required to provide a cure. The treatment can encompass any known treatment for cancer. Examples include endocrine therapy, a chemotherapy, a targeted therapy or another hormonal therapy. In a specific embodiment, the endocrine therapy comprises tamoxifen, raloxifene, megestrol, or toremifene. In a further specific embodiment, the targeted therapy comprises lapitinab, bevacizumab, trastuzumab, cetuximab, or panitumumab. In a further specific embodiment, another hormonal therapy is an aromatase inhibitor such as anastrozole, letrozole, or exemestane, or pure anti-estrogens such fulvestrant, or surgical or medical means (goserelin, leuprolide). In one specific embodiment the treatment is treatment with an ErbB2-targeted drug.

The phosphorylation status of Scribble, or a fragment or variant thereof, can be used to assess how aggressive a particular cancer or tumour is. Such information is very valuable to a clinician, particularly after conducting surgery to remove the primary tumour. Information on how aggressive the cancer or tumour is can be used to determine whether a secondary treatment (following surgery) is required. Such a secondary treatment may be any of the treatments listed above, in particular chemotherapy or radiotherapy. Therefore, in one embodiment, detecting the phosphorylation status of Scribble or a fragment or variant thereof can be used to decide whether chemotherapy is given following surgery.

The invention also relates to methods for assessing the aggressiveness of a tumor comprising assessing the phosphorylation status of the Scribble protein, a fragment or variant thereof. The term "aggressive" or "invasive" with respect to cancer refers to the proclivity of a tumor for expanding beyond its boundaries into adjacent tissue. Invasive cancer can be contrasted with organ-confined cancer wherein the tumor is confined to a particular organ. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located.

The invention also relates to a method for monitoring the effectiveness of a treatment, wherein the method comprises detecting the phosphorylation status of a Scribble protein, a fragment or variant thereof, and determining the effectiveness of a treatment. The phosphorylation status of Scribble can be monitored over the course of a treatment period. As the phosphorylation status provides an indication of the metastatic state or aggressiveness of cancer or tumour, monitoring Scribble phosphorylation over the course of a treatment can indicate how effective the treatment is. In one embodiment the treatment is an anti-metastatic treatment. In this method, the test sample is from a patient who has received or is receiving treatment.

In one embodiment, a method for monitoring the effectiveness of a treatment comprises the steps of (i) optionally obtaining a pre-treatment sample from a patient prior to administration of the treatment; (ii) optionally detecting or measuring the phosphorylation status of Scribble in the pre-treatment sample; (iii) obtaining one or more post-treatment samples from the subject at selected time intervals; (iv) detecting the phosphorylation status of Scribble in the post-treatment samples; (v) comparing the phosphorylation status of Scribble in the pre-treatment sample with the phosphorylation in the post-treatment sample or samples and between different time intervals; and (vi) optionally altering the administration of the treatment to the subject accordingly. For example, no change or a decrease in the phosphorylation status of Scribble during the course of treatment may indicate ineffective dosage and the desirability of increasing the dosage. Conversely, an increase in the phosphorylation status of Scribble may indicate efficacious treatment and thus there is no need to change dosage.

In all the methods described above, a key step is detecting the phosphorylation status of the Scribble protein, or a fragment of variant thereof. In one embodiment detecting or measuring the phosphorylation status means detecting whether the protein is phosphorylated or not phosphorylated. In other embodiments it can mean detecting whether, when considering all potential phosphorylation sites (i.e. a phosphorylation site is a serine or threonine residue) more sites are phosphorylated or more sites are unphosphorylated. A ratio of phosphorylated to unphosphorylated sites can thus be established and this can be indicative of diagnosis, prognosis or treatment. In an alternative embodiment, detecting the phosphorylation status may comprise detecting whether specific residues (i.e. amino acids) within the protein are phosphorylated or not phosphorylated.

In a preferred embodiment, the method comprises detecting the phosphorylation status of at least one of the following residues S1306, S1309, S1348 and S1448 or any combination thereof.

In alternative embodiment, the method comprises detecting the phosphorylation of S1306, S1309, S1348 and S1448.

In a further alternative embodiment, the method comprises detecting the phosphorylation of one of the following:
a. S1306, S1309 and S1348;
b. S1306 and S1309;
c. S1348;
d. S1348 and S1309;
e. S1348 and S1306;
f. S1448 and S1309;
g. S1448 and S1306;
h. S1348 and S1448; or
i. S1306, S1348 and S1448
j. S1309, S1348 and S1448; or
k. S1306, S1309 an S1448.

In a preferred embodiment, the method comprises detecting the phosphorylation of one of a, b or c above.

In an alternative embodiment, the method does not comprise detecting the phosphorylation of S1448.

In a further embodiment, the methods may comprise detecting the phosphorylation status at least one of the following residues S1295. S1298, S1300, T1329, S1330, T1342, S1353, S1445 or combination thereof. The phosphorylation status of any one of these residues or combination thereof may be detected alone or in combination with any of the above described residues or combination of residues.

In a further embodiment to the above, the methods comprise detecting the phosphorylation of only one, more or all the above-described sites. In other words, no other sites are analysed.

Detection of the phosphorylation status of the protein, preferably at one or more of the above-described residues is used in any of the described methods. Hypophosphorylation of Scribble is indicative of a presence or increased aggressiveness of cancer. For example
i. diagnosis of cancer;
ii. detecting metastasis of a cancer;
iii. evaluating the prognosis of a cancer;
iv. selecting a treatment for the treatment of cancer;
v. selecting a subject for treatment;
vi. monitoring the effectiveness of a treatment and/or
vii. assessing the aggressiveness of a tumor.
any one of the following outcomes:
i. a positive diagnosis for cancer;
ii. an indication that a cancer or tumour has metastasised;
iii. a poor prognosis for cancer;
iv. a cancer treatment is selected;
v. a subject for treatment selected;
vi. a treatment is found not to be effective and/or
vii. aggressiveness of a tumor is found to be increased
is reached if the protein is unphosphorylated. In an alternative embodiment, any one of the above outcomes is reached if the number of dephosphorylated sites is greater than the number of phosphorylated sites. In preferred embodiments, any one of the above outcomes is reached if at least one of the following sites are dephosphorylated S1306, S1309, S1348 and S1448, or any combination thereof.

In a further preferred embodiment, any one of the above outcomes is reached if the following residues are dephosphorylated: S1306, S1309, S1348 and S1448. In an alternative embodiment, the following residues are dephosphorylated S1306, S1309 and S1348. In an alternative embodiment, the residues listed in any of the combinations a to k above are dephosphorylated. Preferably, the following residues S1306 and S1309 are dephosphorylated. In a further alternative embodiment the following residue is dephosphorylated S1348.

In a further embodiment, any one of the above outcomes is reached if the following residues are dephosphorylated: 51295. S1298, S1300, T1329, S1330, T1342, S1353, S1445 or combination thereof (including a combination with the above described residues: S1306, S1309, S1348 and S1448).

In a further embodiment no other residues in the protein, or fragment or variant thereof are phosphorylated.

In a further embodiment of the methods described herein, the methods further comprise obtaining a test sample from the patient.

The term 'sample' or 'test sample' as used herein refers preferably to any cell based sample. In a preferred embodiment the sample is tissue, lymph nodes or whole blood. Preferably, the test sample is a tumor sample. Preferably, the sample is a tumor tissue sample. The methods described herein also include providing multiple samples from a subject. Samples can be taken, days, weeks, or months apart from one another.

Tissue or cell samples can be removed from almost any part of the body. The most appropriate method for obtaining a sample depends on the type of cancer that is suspected or diagnosed. Biopsy methods include needle, endoscopic, and excisional. In one embodiment the sample may be a tissue sample comprising cancer cells, where the tissue can be fixed, paraffin-embedded or fresh or frozen. In a further embodiment the tissue sample is obtained by fine needle, core or other type of biopsy.

In a further embodiment of the methods described herein, the phosphorylation status of Scribble, a fragment or variant thereof in the subject's test sample is assessed and compared with the phosphorylation status of Scribble, a fragment or variant thereof in a control sample. Thus, in the methods of diagnosis or prognosis described herein, the method comprises
a) obtaining a biological test sample from a test subject
b) measuring or determining the phosphorylation status of Scribble, a fragment or variant thereof in the test sample
c) comparing the observed phosphorylation status of Scribble to a predetermined test value wherein said predetermined test is based on the phosphorylation status of Scribble in a control sample, for example a sample obtained from an individual patient or population of individuals that are believed not to have cancer and wherein a change in the phosphorylation status of Scribble indicates the presence or increased aggressiveness of cancer. In particular, as explained below, a reduction in the phosphorylation status of Scribble indicates the presence or increased aggressiveness of cancer.

As used herein, a lower level of phosphorylation in the test sample as compared to the level in the control sample refers to an amount or status of phosphorylation of Scribble that is lower than an amount of phosphorylation of Scribble present in a control sample.

The control sample is taken from a reference cohort, that is one or more subject of the same species (e.g., human subjects). The reference cohort are preferably healthy subjects. The individual members of a reference cohort may also share other similarities, such as similarities in stage of disease, previous treatment regimens, lifestyle (e.g., smokers or non-smokers, overweight or underweight), or other demographics (e.g., age, genetic disposition).

The phosphorylation status of Scribble can be measured and compared with a predetermined reference value. The 'predetermined reference value' or 'threshold concentration' (these terms are used interchangeably herein) can be established by skilled healthcare practitioners. For instance, the predetermined reference value can be established by measuring the levels of the biomarker in a normal population sample and correlating such levels with factors such as the incidence, severity, and/or frequency of developing ovarian cancer, more specifically, epithelial ovarian cancer. Thus, a subject's phosphorylation status of Scribble as compared against the phosphorylation status of Scribble in a normal population can be indicative of whether the subject has ovarian cancer. Further, the predetermined reference value is preferably established by using the same assay technique as is used for measurement of the subject's biomarker level, to avoid any error in standardization.

In a further aspect of the methods described herein, detecting the phosphorylation of Scribble, or a fragment or variant thereof, comprises contacting the sample with at least one binding agent, such as an antibody, that is capable of specifically binding at least one phosphorylated or unphosphorylated residue of Scribble. Preferably, the antibody is capable of specifically binding at least one phosphorylated or unphosphorylated residue selected from S1306, S1309, S1348 and S1448 or a combination thereof. Preferably, the antibody is a phospho-antibody.

In the embodiments of this invention where one uses antibodies against Scribble for diagnostic purposes, one can select any immunogenic fragment of Scribble peptides to raise an antibody as is well known to one skilled in the art. The fragments that are immunogenic will lead to generation of antibodies. Scribble fragments can be readily screened for immunogenic activity. Preferably, one uses monoclonal antibodies, but one can also use polyclonal antibodies. One can perform an immunohistochemical analysis using a polyclonal or monoclonal antibody raised against the entire Scribble peptide, or any fragments thereof.

In a further embodiment, the method further comprises determining whether the antibody has bound to the protein—i.e. whether an antibody-antigen complex has formed. In one embodiment, the formation of an antibody-antigen complex is measured using an ELISA. Alternatively bound antibody can be detected using any method known in the art. Examples include 2D gels and ID SDS-PAGE followed by western blotting, dot-blots, and flow cytometry. In an alternative embodiment, bound antibody is detected by in situ analysis of the sample using immunohistochemical staining.

Accordingly, the methods further comprise detection or quantitation of the antigen-antibody complex. Such methods would be well known to the skilled person. For example, any chemical that detects antigen-antibody binding may be used in the practice of the invention. In some embodiments, the detection chemicals comprise a labelled polymer conjugated to a secondary antibody. For example, a secondary antibody that is conjugated to an enzyme that catalyses the deposition of a chromogen at the antigen-antibody binding site may be provided. Such enzymes and techniques for using them in the detection of antibody binding are well known in the art. In one embodiment the secondary antibody that is conjugated to an HRP-labelled polymer. Alternatively, the antigen-antibody complex can be detected using any commercial antibody binding detection system. Examples include BIO-PLEX by Bio-Rad and fluorescent labels.

Embodiments of the methods of the invention involve (a) contacting a test sample from a subject with a binding agent specific for Scribble phosphorylation, e.g. an antibody as described herein, which is directly or indirectly labeled with an enzyme; (b) adding a substrate for the enzyme wherein the substrate is selected so that the substrate, or a reaction product of the enzyme and substrate, forms fluorescent complexes; (c) quantitating Scribble phosphorylation in the sample by measuring fluorescence of the fluorescent complexes; and (d) comparing the quantitated levels to that of a standard.

A another embodiment of the invention comprises the following steps:
(a) incubating a test sample with a first antibody specific for Scribble phosphorylation which is directly or indirectly labeled with a detectable substance, and a second antibody specific for Scribble phosphorylation which is immobilized;
(b) separating the first antibody from the second antibody to provide a first antibody phase and a second antibody phase;

(c) detecting the detectable substance in the first or second antibody phase thereby quantitating Scribble phosphorylation in the biological sample; and (d) comparing the quantitated Scribble phosphorylation with a control.

In a further aspect, the invention provides an antibody capable of selectively binding to at least one phosphorylated residue or at least one dephosphorylated residue in a Scribble protein, or fragment or variant thereof, wherein said residue is selected from S1306, S1309, S1348 and S1448 or a combination thereof.

The term 'antibody' as used herein refers to any immunolglobulin, preferably a full-length immunoglobulin. Preferably, the term covers monoclonal antibodies, polyclonal antibodies, multispecific antibodies, such as bispecific antibodies, intracellular antibodies (or intrabodies) and antibody fragments thereof, so long as they exhibit the desired biological activity. Antibodies may be derived from any species, but preferably are of rodent, for examples rat or mouse, human or rabbit origin. Alternatively, the antibodies, preferably monoclonal antibodies, may be humanised, chimeric or antibody fragments thereof. The term 'chimeric antibodies' may also include "primatised" antibodies comprising variable domain antigen-binding sequences derived from a non-human primate (e.g., Old World Monkey, Ape etc) and human constant region sequences. The immunoglobulins can also be of any type (e.g. IgG, IgE, IgM, IgD, and IgA), class (e.g., IgG1, IgG2, IgG3, IgG4, IgA1 and IgA2) or subclass of immunoglobulin molecule.

The term 'monoclonal antibody' refers to a substantially homogenous population of antibody molecules (i.e. the individual antibodies comprising the population are identical except for possible naturally occurring mutations that may be present in minor amounts), produced by a single clone of B lineage cells, often a hybridoma. Importantly, each monoclonal has the same antigenic specificity—i.e. it is directed against a single determinant on the antigen.

The production of monoclonal antibodies can be carried out by methods known in the art. However, as an example, the monoclonal antibodies can be made by the hybridoma method (Kohler et al (1975) Nature 256:495), the human B cell hybridoma technique (Kozbor et al., 1983, Immunology Today 4: 72), or the EBV-hybridoma technique (Cole et al., 1985, Monoclonal Antibodies and Cancer Therapy, Alan R. Liss, Inc., pp. 77-96). Alternatively, the monoclonal antibody can be produced using recombinant DNA methods (see, U.S. Pat. No. 4,816,567) or isolated from phage antibody libraries using the techniques described in Clackson et al (1991) Nature, 352:624-628; Marks et al (1991) J. Mol. Biol., 222: 581-597.

Polyclonal antibodies are antibodies directed against different determinants (epitopes). This heterogenous population of antibody can be derived from the sera of immunised animals using various procedures well known in the art.

The term 'bispecific antibody' refers to an artificial antibody composed of two different monoclonal antibodies. They can be designed to bind either to two adjacent epitopes on a single antigen, thereby increasing both avidity and specificity, or bind two different antigens for numerous applications, but particularly for recruitment of cytotoxic T- and natural killer (NK) cells or retargeting of toxins, radionuclides or cytotoxic drugs for cancer treatment (Holliger & Hudson, Nature Biotechnology, 2005, 9, 23). The bispecific antibody may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al., Methods in Enzymology, 1986, 121:210; Rodrigues et al., 1993, J. of Immunology 151:6954-6961; Carter et al., 1992, Bio/Technology 10:163-167; Carter et al., 1995, J. of Hematotherapy 4:463-470; Merchant et al., 1998, Nature Biotechnology 16:677-681.

Methods to prepare hybrid or bispecific antibodies are known in the art. In one method, bispecific antibodies can be produced by fusion of two hybridomas into a single 'quadroma' by chemical cross-linking or genetic fusion of two different Fab or scFv modules (Holliger & Hudson, Nature Biotechnology, 2005, 9, 23).

The term 'chimeric' antibody refers to an antibody in which different portions are derived from different animal species. For example, a chimeric antibody may derive the variable region from a mouse and the constant region from a human. In contrast, a 'humanised antibody' comes predominantly from a human, even though it contains non-human portions. Specifically, humanised antibodies are human immunoglobulins (recipient antibody) in which residues from a hypervariable region of the recipient are replaced by residues from hypervariable regions of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanised antibodies may comprise residues that are not found in the recipient antibody or in the donor antibody. These modifications are made to further refine antibody performance. In general, the humanised antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanised antibody optionally also will comprise at least a portion of an immunoglobulin constant region (Fc), typically that of a human immunoglobulin.

Recombinant antibodies such as chimeric and humanised monoclonal antibodies can be produced by recombinant DNA techniques known in the art. Completely human antibodies can be produced using transgenic mice that are incapable of expressing endogenous immunoglobulin heavy and light chains genes, but which can express human heavy and light chain genes. The transgenic mice are immunized in the normal fashion with a selected antigen. Monoclonal antibodies directed against the antigen can be obtained using conventional hybridoma technology. The human immunoglobulin transgenes harboured by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, for example, U.S. Pat. Nos. 5,625,126; 5,633, 425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

The term 'antigen-binding fragment' in the context of the present invention refers to a portion of a full length antibody where such antigen-binding fragments of antibodies retain the antigen-binding function of a corresponding full-length antibody. The antigen-binding fragment may comprise a portion of a variable region of an antibody, said portion comprising at least one, two, preferably three CDRs selected from CDR1, CDR2 and CDR3. The antigen-binding fragment may also comprise a portion of an immunoglobulin light and heavy chain. Examples of antibody fragments include Fab, Fab', F(ab')2, scFv, di-scFv, and BiTE (Bi-specific T-cell engagers), Fv fragments including nanobodies, diabodies, diabody-Fc fusions, triabodies and, tetrabodies; minibodies; linear antibodies; fragments produced by a Fab expression library, anti-idiotypic (anti-Id) antibodies, CDR (complementary determining region), and epitope-binding fragments of any of the above that immunospecifically bind to a target antigen such as a cancer cell antigens, viral antigens or microbial antigens, single-chain or single-domain antibody molecules including heavy chain only antibodies, for example, camelid VHH domains and shark V-NAR; and multispecific antibodies formed from antibody fragments. For comparison, a full length antibody, termed 'antibody' is one comprising a VL and VH domains, as well as complete light and heavy chain constant domains.

The antibody may also have one or more effector functions, which refer to the biological activities attributable to the Fc region (a native sequence Fc region or amino acid sequence variant Fc region engineered according to methods in the art to alter receptor binding) of an antibody. Examples of antibody effector functions include Clq binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

The antibody can also be a functionally active fragment, derivative or analog of an antibody that immunospecifically binds to a target antigen such as a cancer cell antigen, viral antigen, or microbial antigen or other antibodies bound to tumour cells. In this regard, functionally active means that the fragment, derivative or analog is able to elicit anti-idiotype antibodies that recognise the same antigen that the antibody from which the fragment, derivative or analog is derived recognised. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay), see, for example, Kabat et al., 1991, Sequences of Proteins of Immunological Interest, Fifth Edition, National Institute of Health, Bethesda, Md.; Kabat E et al., 1980, J. of Immunology 125(3):961-969).

The term 'antibody' may also include a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Furthermore, the antibody or antigen-binding fragments of the present invention may include analogs and derivatives of antibodies or antigen-binding fragments thereof that are either modified, such as by the covalent attachment of any type of molecule as long as such covalent attachment permits the antibody to retain its antigen binding immunospecificity. Examples of modifications include glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies or antigen-binding fragments of the present invention may also have modifications (e.g., substitutions, deletions or additions) in the Fc domain of the antibody. Specifically, the modifications may be in the Fc-hinge region and result in an increased binding for the FcRn receptor (WO 97/34631).

In another embodiment, the phosphorylation status of the scribble protein, a fragment or variant thereof is assessed using mass spectrometry techniques.

Prolonged expression of CD74 has also been demonstrated to lead to a decrease in expression levels of Scribble. Accordingly, in a further aspect, the methods described herein include measuring and detecting a decrease in the expression levels of Scribble. In a further embodiment, the methods described herein may include measuring both the phosphorylation status and expression levels of Scribble. In one embodiment dephosphorylation of Scribble or a fragment or variant thereof, or more preferably, dephosphorylation of one of the specific residues described herein and a decrease in the expression levels is indicative of cancer, metastasis of cancer, a poor prognosis and/or affect whether a patient is selected for treatment or the choice of treatment for the patient and is indicative of whether a treatment is effective.

In an alternative embodiment, any of the methods described herein can be used in combination with assessment of conventional clinical factors (e.g. tumour size, tumour grade, lymph node status and family history) and/or analysis of other molecular markers, for example analysis of the expression level of a second or more molecular marker. Such marker could be a biomarker involved in cell cycle regulation, DNA replication, transcription, signal transduction, cell proliferation, invasion or metastasis. Examples of such markers include EGFR, Her2/neu, Ki67, p53, estrogen and progesterone hormone. In this manner the methods of the invention permit a more accurate evaluation of cancer prognosis. Thus, one aspect of the invention, a secondary diagnostic step can be performed. For example, if a level of phosphorylation of Scribble or a fragment or variant thereof is found to indicate the presence or aggressiveness of cancer, then an additional method of detecting the cancer can be performed to confirm the presence of the cancer. Any of a variety of additional diagnostic steps can be used, such as mammography (breast cancer), ultrasound, PET scanning, MRI, or any other imaging techniques, biopsy, clinical examination, ductogram, or any other method.

Kits for practicing the methods of the invention are further provided. A 'kit' refers to any manufacture (e.g., a package or a container) comprising at least one reagent, e.g. a binding agent such as an antibody, for specifically detecting the phosphorylation status of Scribble. The kit may be promoted, distributed, or sold as a unit for performing the methods of the present invention. Additionally, the kits may contain a package insert describing the kit and methods for its use. The kit may also comprise a solid support such as microtiter multi-well plates.

For example, the kit can contain reagents, tools, and instructions for determining an appropriate therapy for a cancer patient. Such a kit can include reagents for collecting a tissue sample from a patient, such as by biopsy, and reagents for processing the tissue. The kit can also include one or more reagents for detecting the phosphorylation status of Scribble. In one embodiment, the kit may also comprise one or more reagents for performing a gene expression analysis, such as reagents for performing RT-PCR, Northern blot, Western blot analysis, or immunohistochemistry to determine scribble expression levels in a tumor sample. Appropriate buffers for the assays can also be included.

A kit can contain separate containers, dividers or compartments for the reagents and informational material.

In particular embodiments, kits for practicing the methods of the invention are provided. Such kits are compatible with both manual and automated immunohistochemistry techniques (e.g., cell staining). These kits comprise at least one antibody capable of specifically detecting the phosphorylation status of Scribble. Chemicals for the detection of antibody binding to Scribble, a counterstain, and a bluing agent to facilitate identification of positive staining cells are optionally provided. Alternatively, the immunochemistry kits of the present invention are used in conjunction with commercial antibody binding detection systems, such as, for example the BIOPLEX assay by Bio-Rad. Any chemicals that detect antigen-antibody binding may be used in the practice of the invention. In some embodiments, the detection chemicals comprise a labelled polymer conjugated to a secondary antibody. For example, a secondary antibody that is conjugated to an enzyme that catalyses the deposition of a chromogen at the antigen-antibody binding site may be provided. Such enzymes and techniques for using them in the detection of antibody binding are well known in the art. In one embodiment, the kit comprises a secondary antibody that is conjugated to an HRP-labeled polymer. Chromogens compatible with the conjugated enzyme (e.g., DAB in the case of an HRP-labeled secondary antibody) and solutions, such as hydrogen peroxide, for blocking non-specific staining may be further provided. The kits of the present invention may also comprise a counterstain, such as, for example, hematoxylin. A bluing agent (e.g., ammonium hydroxide) may be further provided in the kit to facilitate detection of positive staining cells.

In another embodiment, the immunohistochemistry kits of the invention comprise at least two reagents, e.g., antibodies, for specifically detecting the phosphorylation status of Scribble, or a fragment or variant thereof. Preferably, each antibody is capable of specifically binding a different residue on Scribble. Preferably, each antibody is capable of binding to a different residue selected from S1306, S1309, S1348 and S1448. Each antibody may be provided in the kit as an individual reagent or, alternatively, as an antibody cocktail comprising all of the antibodies directed to the different biomarkers of interest. Furthermore, any or all of the kit reagents may be provided within containers that protect them from the external environment, such as in sealed containers. Positive and/or negative controls may be included in the kits to validate the activity and correct usage of reagents employed in accordance with the invention. Controls may include samples, such as tissue sections, cells fixed on glass slides, etc., known to be either positive or negative for Scribble phosphorylation. The design and use of controls is standard and well within the routine capabilities of those of ordinary skill in the art.

In other embodiments, kits for practicing the methods of the invention are provided, wherein the kit includes at least one antibody for the detection of Scribble phosphorylation status and one means for detecting expression levels of Scribble. Such kits comprise, for example, at least one nucleic acid probe that specifically binds to a Scribble nucleic acid or a fragment or variant thereof. In an alternative embodiment, the means for detecting expression levels of Scribble can comprise measuring protein levels of Scribble. Examples include immunohistochemistry or western blot or any other proteomics technique.

In another aspect of the invention I describe a method of treating cancer, wherein the method comprises administering a therapeutically effective amount of an agent capable of phosphorylating or preventing the dephosphorylation of a Scribble protein, or fragment or variant thereof. Preferably the agent is capable of phosphorylating or preventing the dephosphorylation of at least one residue in a Scribble protein, fragment or variant thereof, wherein said residue is selected from S1306, S1309, S1348 and S1448 or a combination thereof. In one example, the agent is kinase. In particular the agent may be an ERK map kinase. Preferably the kinase is specific to Scribble, or specifically phosphorylates at least one residue selected from S1306, S1309, S1348 and S1448 or a combination thereof. Alternatively, the agent may be a phosphatase. In one example, the phosphatase is PP2A. Again, preferably the phosphatase is specific to Scribble, or more preferably specific for at least one residue selected from S1306, S1309, S1348 and S1448 or a combination thereof. In order to achieve this specificity the kinase or phosphatase may be genetically modified. In a further alternative, the agent may be a vector capable of expressing a mutated Scribble protein, or fragment or variant thereof, wherein at least one of the following residues, S1306, S1309, S1348 and S1448, mimic the constitutively phosphorylated state, or are incapable of being dephosphorylated.

By 'therapeutically effective amount' of an agent it is meant an amount of active agent that is capable of preventing or at least slowing down (lessening) cancer cell migration or metastases. Dosages and administration of an agent of the invention in a pharmaceutical composition may be determined by one of ordinary skill in the art of clinical pharmacology or pharmacokinetics. An effective amount of the antagonist to be employed therapeutically will depend, for example, upon the therapeutic objectives, the route of administration, and the condition of the mammal. Accordingly, it will be necessary for the therapist to titre the dosage and modify the route of administration as required to obtain the optimal therapeutic effect. A typical daily dosage might range from about 10 ng/kg to up to 100 mg/kg of the mammal's body weight or more per day, preferably about 1 pg/kg/day to 10 mg/kg/day. Doses may include an antibody amount anywhere in the range of 0.1 to 20 mg/kg of bodyweight or more preferably 1, 5, 10 mg/kg of bodyweight.

Thus, the present invention also relates to pharmaceutical compositions comprising a therapeutically effective amount of an agent capable of phosphorylating or preventing the dephosphorylation of Scribble, preferably at least one of the residues S1306, S1309, S1348 and S1448, and a pharmaceutically acceptable carrier.

Pharmaceutical forms of the invention suitable for injectable use, include sterile aqueous solutions such as sterile phosphate-buffered saline (where water soluble) or dispersions and sterile powders for the extemporaneous preparation of sterile injectable solutions and or one or more carrier. Alternatively, injectable solutions may be delivered encapsulated in liposomes to assist their transport across cell membrane. Alternatively or in addition such preparations may contain constituents of self-assembling pore structures to facilitate transport across the cellular membrane. It must be stable under the conditions of manufacture and storage and must be preserved against the contaminating/destructive action of microorganisms such as, for example, bacteria and fungi.

The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as, for example, lecithin, by the maintenance of the required particle size in the case of dispersion and by the use of surfactants. Preventing the action of microorganisms in the compositions of the invention is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and freeze-drying, to yield a powder of the active ingredient plus any additional desired ingredient from previously sterile-filtered solution thereof.

The active ingredient may be held within a matrix which controls the release of the active agent. Preferably, the matrix comprises a substance selected from the group consisting of lipid, polyvinyl alcohol, polyvinyl acetate, polycaprolactone, poly(glycolic)acid, poly(lactic)acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly(ortho esters), sucrose acetate isobutyrate (SAIB), and combinations thereof and other polymers.

Pharmaceutically acceptable carriers and/or diluents may also include any and all solvents, dispersion media, coatings, antibacterials and/or antifungals, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated.

In a further aspect of the invention I describe a method of selecting or excluding a subject for enrolment in a clinical trial or stratifying a subject population for analysis of a clinical trial, the method comprising detecting the phosphorylation status of a Scribble protein, or fragment or variable thereof, in a sample from at least one subject and selecting or excluding a subject or stratifying a subject population based on the phosphorylation of Scribble.

A further aspect of the invention relates to a diagnostic device useful in carrying out the methods of the invention can be constructed in any form adapted for the intended use. In one embodiment, the device of the invention comprises a solid support (such as a strip or dipstick), with a surface that functions as a lateral flow matrix defining a flow path for a biological sample such as whole blood. The invention also relates to a immunochromatographic assay for the diagnosis of cancer comprising one or more immobilized antibody for the detection of the phosphorylation status of Scribble, a fragment or variant thereof.

In a final aspect of the invention I describe a method of visualising or determining the intracellular localisation of Scribble in a cell, particularly an apical or basolateral location, the method comprising administering an antibody capable of binding at least one phosphorylated or unphosphorylated residue in Scribble selected from S1306, S1309, S1348 and S1448 or combination thereof, wherein the antibody is further conjugated to a reporter. In one embodiment the reporter is luminescent or fluorescent.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the multiple specified features or components with or without the other at each combination unless otherwise dictated. For example "A, B and/or C" is to be taken as specific disclosure of each of (i) A, (ii) B, (iii) C, (iv) A and B, (v) B and C or (vi) A and B and C, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

EXAMPLE I

Materials and Methods

Unless indicated otherwise in the text, chemicals and HPLC solvents were purchased from Thermo Fisher (Loughborough, United Kingdom). The highest available grades were used.

Cell Culturing

Breast cancer cell lines MDA-MB-435, MDA-MB-231, MCF7, and ZR-75.1 and human embryonic kidney 293T/s (HEK293T/s) were grown on RPMI 40 Ultraglutamine medium supplemented with 10% fetal calf serum at 37° C. and 5% $CO_2$ and split every second day. The cells were grown to about 80% confluency, detached, washed with phosphate-buffered saline (PBS), and stored at −80° C. until needed for analysis.

SILAC Labeling

The cell cultures were labeled using the SILAC Labeling Kit from Thermo Fisher following the manufacturer's instructions and as described by Ong et al. [13]. All cell cultures were labeled for at least five doubling times to ensure complete protein labeling.

Transient Transfection

This was performed as previously described using HEK293T and MCF7 cells [5].

Generation of Stably Transfected HEK293s Cells Expressing CD74 under the Tetracycline-Inducible Promoter To generate these cell lines, I used an HEK293s derivative stably transfected with the TetR construct and expressing the repressor (HEK293s-TetR) [14]. The cells and the TetO plasmid were kind gifts from Dr Phil Reeves from the University of Essex. The CD74 sequence was subcloned into the TetO plasmid using the following primers:

```
FOR:
                                       SEQ ID NO: 2
5'-GGAATTCGCCACCATGCACAGGAGGAGAAGCAG-3':

REV:
                                       SEQ ID NO: 3
5'-GCGGCCGCTCACATGGGGACTGGGCCCAGATCC-3':
``` from a construct described previously and using the same cloning strategy as described by Reeves et al. for rhodopsin [14]. The TetOCD74 plasmid was sequenced to validate the sequence and then transfected in to the HEK293s-TetR cells. The transfectants were selected on G418-containing medium for about 3 weeks until G418-resistant TetR/TetO colonies could be isolated. Twelve colonies were isolated initially, and after screening for inducible CD74 expression, five positive colonies were expanded and stored as stock for further experiments.

CD74 Overexpression and Knockdown

The TetR/TetO-CD74 HEK293s cells were induced with 1 µg/ml tetracycline for various periods of time. An untreated TetR/TetOCD74 control was mock treated for the same periods of time. An additional control with TetR HEK293s cells treated with tetracycline was also included in most of the experiments to identify possible tetracycline-induced phenomena that are independent of CD74. CD74 knockdown in MDA-435-MB cells was performed using siRNA from Santa Cruz Biotechnology (Santa Cruz, Calif.) according to the manufacturer's instruction.

Tumor Tissue Acquisition

All tissues were collected under Local Research Ethics Committee (LREC) and National Health Services (NHS) Trust approval as previously described [5,15]. Tumor tissue was placed on ice immediately in the operating theater. The tissue was assessed and cut by the pathologist on ice before being divided up with a proportion of the tissue snap frozen in liquid nitrogen and the remainder fixed in formalin with the shortest possible delay.

Membrane Protein Isolation

Approximately 20 to 50 mg of frozen tissue from a surgery specimen or core biopsy was snap frozen in liquid nitrogen and pulverized in a BioPulverizer stainless steel device (BioSpec Products, Bartlesville, Okla.). The homogenized sample was placed on ice and mixed with 500 µl of permeabilization solution containing PBS, 0.2% saponin, and protease and phosphatase inhibitors (Roche Diagnostics, Burgess Hill, United Kingdom). For cultured cells, the homogenization step was omitted and the cells were directly permeabilized. The samples were incubated on ice with intermittent mixing for 15 minutes and centrifuged at 14,000 rpm in a refrigerated centrifuge for 45 minutes. Following centrifugation, the supernatant containing the water-soluble proteins was removed and stored frozen until needed. The pellet was washed with 500 µl of PBS containing protease and phosphatase inhibitors and centrifuged as above. The washed permeabilized pellet was extracted with 100 µl of membrane protein extraction buffer containing 1% (vol/vol) IGEPAL in 50 mM Tris-HCl (pH 7.4), 150 mM NaCl, and protease and phosphatase inhibitors as above, resuspended, and incubated on ice for 10 to 15 minutes. Cultured cells were extracted in 1 ml of buffer per 107 cells. The sample was then centrifuged at 4° C. and 14,000 rpm for 15 minutes. The supernatant containing the membrane proteins was recovered and either processed immediately as described below or stored at −80° C. until needed.

Immunoprecipitation

Membrane protein fractions extracted as above containing about 0.5 mg of total protein (estimated by dye-binding assay) were diluted 1:1 with binding buffer containing 50 mM Tris-HCl (pH 7.4) and 150 mM NaCl and incubated with 6 µg of LN2 antibody for 30 minutes at room temperature to allow antibody binding to the CD74 extracellular domain. To each tube, 60 µl of protein NG agarose (Santa Cruz Biotechnology) prewashed with 1 ml of binding buffer was then added. The tubes were further incubated for 1 hour at room temperature on a rotator. I found that because of the inclusion of protease and phosphatase inhibitors in the membrane extraction buffer, performing the experiments at room temperature gave better yields and throughput. The agarose beads were washed three times with binding buffers and the precipitated proteins eluted with 30 µl of sodium dodecyl sulfate sample buffer containing 12 mM DTT for 5 minutes at 100° C. The samples were then cooled on ice and alkylated with 60 mM iodoacetamide for 30 minutes in the dark. For Western blot analysis, an aliquot of the sample was separated by denaturing polyacrylamide gel electrophoresis (PAGE) and transferred onto a polyvinylidene fluoride (PVDF) membrane. For immunoprecipitation/mass spectrometry (IP/MS) analysis, the sample was separated and the gel sliced into five size-resolved fractions, digested with trypsin, and analysed by liquid chromatography/tandem mass spectrometry (LC-MS/MS).

Protein Digestion and Preparation of Samples for Mass Spectrometry

The protein samples were mixed with 2× sodium dodecyl sulphate sample buffer, reduced, alkylated, and subjected to in-gel digestion as previously described [15]. The SILAC-labeled proteins were separated into up to 10 fractions by a semipreparative PAGE before digestion.

Isolation of Phosphopeptides

Aliquots containing about 0.5 mg of total protein were separated by a semipreparative PAGE on single-well minigel. Up to 10 size-resolved fractions were excised and digested as described above. The tryptic peptides were extracted from the gel pieces, and 10% of the extracted peptides were removed for quantitative analysis of protein abundance and dried in a vacuum concentrator. The remaining 90% were also dried and dissolved in 100 µl of 80% acetonitrile containing 2% formic acid and used to isolate phosphorylated peptides. Phosphopeptides were isolated using the Magnetic TiO2 Phosphopeptide Isolation Kit from Thermo Fisher following the manufacturer's instructions.

Nanoscale LC-MS/MS Analysis

Protein digest analysis by electrospray ionization MS was performed on a hybrid LTQ/Orbitrap Velos instrument (Thermo Fisher) interfaced to a splitless nanoscale HPLC (Ultimate 3000; Dionex, Loughborough, United Kingdom). The peptides were desalted and concentrated online at a flow of 1 µl/min on a 2-cm-long, 0.1-mm i.d. trap column packed with 5-µm C18 particles (Dionex). Following concentration/ desalting, the peptides were eluted from the trap column and separated in a 90-minute gradient of 2% to 30% (vol/vol) acetonitrile in 0.1% (vol/vol) formic acid at a flow rate of 0.3 μl/min. The separation column was a 15-cm-long, 0.1-mm i.d. pulled tip packed with 5-μm C18 particles (Nikkyo Technos Co, Tokyo, Japan). The eluting peptides were electrosprayed directly from the packed tip into the LTQ/Orbitrap Velos mass spectrometer by applying 1.75 kV through a liquid junction interface. The LTQ/Orbitrap Velos was operated in the Top 20 data-dependent mode where it first executes two high-resolution scans at a resolution of 30,000 (at 400 m/z) followed by 20 MS/MS scans for the 20 most abundant peptide ions having a charge state>1. During the high-resolution scans, the Orbitrap analyzer was set to accumulate 106 ions for the maximum of 0.5 second. During MS/MS scans, the LTQ was set to accumulate 5000 precursor ions for the maximum of 0.1 second. The normalized collision energy was set to 30; minimum signal intensity required was set to 500, activation time to 10 milliseconds, and activation Q to 0.250. A dynamic exclusion procedure was implemented to avoid repetitive analysis of abundant peptide ions: After a peptide ion has been analysed once, its m/z was put in the exclusion list for 30 seconds. The mass calibration was internal by means of lock mass. The ambient ion of 445.12 m/z was used for this purpose throughout all experiments. For targeted detection of Scribble peptides, a mixed mode analysis was used in which a full scan was performed as described above; the next four selected reaction monitoring (SRM) scans were performed to isolate and fragment two Scribble reporter peptides, VSLVGADDLR (SEQ ID NO: 4) and VQSPEPPAPER (SEQ ID NO:5), in their heavy and light SILAC isoforms. Finally, seven data-dependent MS/MS scans were performed to isolate and fragment the seven most abundant peptide ions detected in the high-resolution full scan.

Data Analysis

MS/MS data were analyzed by MaxQuant and the *Andromeda* search engine as described in [16-18]. The MaxQuant searches were performed using a reverse database to calculate false discovery rate (FDR). Results from the *Andromeda* engine were filtered at both peptide and protein level. In both cases, the cutoff was at 1% FDR. For SILAC ratios of unmodified peptides and phosphopeptides, the quantitative analysis was performed by MaxQuant and further evaluated by statistical tests using Microsoft Excel.

Western Blot Analysis and Immunohistochemical Analysis of Tumor Tissue

Immunoblot analysis and immunohistochemistry were performed as previously described [15]. For CD74 detection in immunohistochemical (IHC) and for immunoprecipitation, the mouse monoclonal antibody LN2 from Santa Cruz Biotechnology was used. β-Tubulin and Scribble antibodies were also from Santa Cruz Biotechnology. IHC staining was scored using the immunoreactivity score (IRS) scores as implemented for Her2 staining, taking into account staining intensity and the percentage of positive cells: intensity ranges from 1 to 3 for weak, moderate, and strong staining, respectively. Percentage ranges from 1 to 5 for <10%, 10% to 25%, 25% to 50%, 50% to 75%, and >75% staining of the malignant cells; total score=intensity+ percentage.

Indirect Immunofluorescence and Colocalization Analysis

Cells to be analyzed were grown in eight-well chamber slides (Lab-Tek; Fisher Scientific, Loughborough, United Kingdom), treated and fixed in 4% buffered paraformaldehyde, and permeabilized in PBS containing 0.5% Triton X-100 for 5 minutes. The cells were blocked in 5% BSA in PBS for 1 hour and stained with mouse anti-Scribble antibody and rabbit anti-CD74 antibody (1:100 dilution) diluted in PBS containing 1% BSA for 1 hour at room temperature (RT). The cells were washed three times in PBS containing 0.1% (vol/vol) Tween 20. The cells were then incubated with secondary antibody solution containing goat anti-mouse Cy5 (Abcam, Cambridge, United Kingdom) and goat anti-rabbit fluorescein isothiocyanate (Abcam), diluted 1:1000 in PBS containing 1% BSA and 0.1% Tween 20 for 45 minutes. The cells were then washed three times in PBS containing 0.1% Tween 20 and analyzed by laser scanning confocal microscopy on a Nikon Eclipse Ti microscope. Colocalized pixels were identified using the ImageJ plugin ColocalizeRGB.

Fluorescence-Activated Cell Sorting (FACS) Analysis

The cells were stained as above and counted in a BD FACS Aria instrument. A secondary antibody-only control was included to estimate nonspecific staining.

Results

In a previous study, I found that CD74 is more abundant in lymph node-metastatic triple-negative tumors compared to nonmetastatic triple-negative breast cancer (TNBC) tumors. This conclusion was based on data obtained by mass spectrometry and pooled tumor protein lysates from six metastatic and six nonmetastatic triple-negative breast tumors [5]. Since this analysis did not discriminate between expression in the malignant cells and other cells in the tumor, I decided to reexamine CD74 expression in another collection of triple-negative breast tumors, this time using immunohistochemical staining instead of mass spectrometry. The results, shown in FIG. 6 confirmed the previously reported observation that CD74 tends to be more abundant in lymph node-metastatic triple-negative breast tumors. I stained 9 nodepositive tumors and 10 node-negative tumors. Seven of the nodepositive tumors showed strong CD74 staining in the malignant cells, while only 3 of the 10 node-negative tumors showed such staining. This corresponds to a P value of 0.0409 by the nonparametric Mann-Whitney t test, indicating that aberrant CD74 expression in the malignant cells is associated with increased metastasis. A similar pattern was observed when various established breast cancer cell lines were studied for CD74 expression: The most metastatic line, MDA-435-MD, was the only one to show constitutive CD74 expression. All other tested cell lines did not express the protein normally at detectable level, although some of them could be induced to express small amounts if treated with interferon γ ([4,5]). To investigate whether CD74 expression contributes to invasion of MDA-435-MB cells, I used siRNA to knock down CD74 and performed wound healing assays. The wound healing assay is a standard assay in the art to measure the ability of cells to migrate and invade, both of which are a very important part of metastasis. Indeed, when the expression of CD74 was downregulated by siRNA, the wound healing ability of MDA-435-MB cells was diminished (FIG. 7). Thus, tumour specimen analysis and in vitro experiments with cultured cells provided additional evidences for the involvement of CD74 in the invasion and metastasis of breast cancer. To identify likely targets of CD74 in this context, I decided to follow a quantitative approach based on stable isotope labelling, in which total protein abundance and protein phosphorylation were quantified simultaneously in cells engineered to express the protein in a highly regulated way. This allowed the identification of phosphorylation hotspots: protein phosphorylation sites that are significantly affected by CD74 overexpression while the corresponding total protein abundances are not. This combined genome-scale proteomic screen pinpointed the tumor suppressor protein Scribble as a likely target of CD74 in breast cancer. While the total amount of Scribble, as measured by quantitative high-resolution mass spectrometry, did not change dramatically after 24 hours of CD74 expression, three specific phosphopeptides decreased significantly in the cells overexpressing CD74. FIGS. 1 and 8 illustrate the results obtained using HEK293s cells expressing CD74 under the control of a tetracycline-inducible promoter. Similar results were obtained in transiently transfected MCF7 cells. Three of the phosphorylation sites on two of the phosphopeptides conform well to the canonical mitogen-activated protein kinase (MAPK) phosphorylation consensus, P-X-S/T-P, and have been detected previously in large-scale phosphoproteomics studies [19,20]. The third peptide is also phosphorylated on a proline-directed site and could be either MAPK or cyclin-directed kinase target. Following the identification of Scribble as likely target of CD74, I examined its intracellular localization in control HEK293T and MCF7 cells and in cells transiently transfected with a construct encoding fulllength CD74. Strikingly, in the transfected cells, Scribble appeared to change its typical localization at the adherence junctions and translocate to the cytoplasm. This is shown in FIG. 2. In the stably transfected HEK293s cells, the protein did not change localization as dramatically after 24 hours of induction, but its immunoreactivity increased and the CD74-expressing cells consistently showed significantly higher fluorescence in confocal images (FIG. 3C). This increased immunoreactivity was reproduced in FACS experiments (FIG. 3B) but not in Western blot analyses (FIG. 3A). To shed more light on the underlying mechanisms, I then asked whether CD74 and Scribble interact and/or colocalize in the stably transfected cells. Binding of CD74 to a particular part of Scribble might, for example, prevent the interaction of Scribble with a third protein and effectively ensure that the epitope recognized by the anti-Scribble antibody is exposed and detectable in immunofluorescence and FACS experiments. Indeed, in both co-IP/Western blot and co-IP/MS experiments, CD74 and Scribble copurified as shown in FIG. 4. I first performed co-IP/Western blot experiments, in which CD74 was immunoprecipitated using an antibody recognizing its extracellular part. The immunoprecipitated proteins were probed with anti-Scribble antibody and a band with the same electrophoretic mobility as Scribble was detected only in the co-IP from cells overexpressing CD74 but not from control uninduced cells (FIG. 4A). To rule out any possibility that this result might have been due to a nonspecific binding or antibody cross-reactivity, I performed independent co-IP/MS experiments. These were again designed around the quantitative SILAC technology; its implementation for protein interaction analysis is described by Blagoev et al. [21] and took advantage of the high sensitivity and mass accuracy of the hybrid LTQ/Orbitrap technology. To ensure quantitative precision and rule out false-positive results, the co-IP/MS experiments were performed twice independently and in the following manner: In the first experiment, I labeled one cell culture with heavy arginine and lysine and had another cell culture grown on light amino acids. I then induced CD74 expression for 24 hours in the heavy-labeled culture but left the light-labeled culture uninduced. Then, CD74 was immunoprecipitated from both cell cultures under identical conditions and using equal total protein amounts. The proteins immunoprecipitated from "heavy" and "light" cultures were mixed, separated by denaturing PAGE, digested with trypsin, and analyzed by high-resolution LC-MS/MS. To increase the sensitivity of detection, I performed a mixed mode data-dependent/targeted analysis. This allowed a very precise quantitative assessment of the ability of CD74 to coimmunoprecipitate Scribble. In the alternative labeling experiment, this procedure was repeated but in reverse: The light-labeled culture was induced with tetracycline, while the heavy-labeled sample was left uninduced. The results from these experiments are shown in FIG. 4B. In both assays, Scribble reporter peptides were only detected in the CD74 IP from the induced samples but not from the uninduced samples. Thus, CD74 and Scribble copurify, which suggests that the two proteins might interact physically, either directly or through a third protein. If this is the case and the interaction takes place in vivo, then subpopulations of CD74 and Scribble molecules should also be seen at the same sites in the cells. I therefore asked whether the two proteins colocalize and performed double-labeling immunofluorescence experiments to test this hypothesis. The results, illustrated in FIG. 4C, show that, indeed, this is the case and portions of the pools of the two proteins clearly colocalize in the CD74-overexpressing cells. In another independent line of investigations, I transfected TetOCD74 HEK293 cells with a green fluorescent protein (GFP)-tagged Scribble construct and asked whether GFP-Scribble would change localization when the expression of CD74 is turned on by tetracycline. The results from these experiments are illustrated in FIG. 5. The GFP-Scribble reporter localized to the basolateral parts of the membrane in the uninduced cells and was never seen on the apical side of the cell. In contrast, when CD74 was overexpressed for 24 hours, GFP Scribble clearly appeared at the apical side of the cells. This was also seen in indirect immunofluorescence experiments, in which I stained endogenous Scribble with a monoclonal antibody as in the experiments presented in FIG. 4 and examined its localization by confocal microscopy.

In recent tumor proteomics study focusing on triple-negative breast cancer, I identified CD74 as frequently overexpressed in the lymph node-metastatic tumors [5].

It was unexpectedly discovered that when CD74 is overexpressed in cultured epithelial and cancer cells, the phosphorylation state of several sites in the C-terminal part of the tumor suppressor protein Scribble changes significantly. The corresponding phosphopeptides were detected and quantified by high-resolution mass spectrometry using SILAC-labeled cells. Altogether, 19 different Scribble phosphorylation sites were mapped and also quantified a large number of unmodified Scribble peptides. This enabled statistical analysis that pinpointed four phosphorylation sites as hotspots—phosphorylations that change significantly in response to CD74 overexpression. Three of these sites conform to the canonical MAPK consensus, which is intriguing as CD74 was previously implicated in an MAPK signaling: As a cellular receptor for the cytokine macrophage inhibitory factor (MIF), CD74 was shown to interact and activate the RAF/mitogen-activated protein kinase kinase (MEK)/extracellular signal-regulated kinase (ERK) cascade [6]. Furthermore, Scribble localization changed and apparent immunoreactivity increased in cells overexpressing CD74 (FIG. 2). Conceivably, there could be at least three explanations for this increased immunoreactivity: 1) Scribble protein abundance might be upregulated in response to CD74 overexpression; 2) the epitope recognized by the anti-Scribble antibody could overlap with and be masked by the MAPK-dependent phosphorylations discussed above, which would mean that overexpression of CD74, by decreasing the phosphorylation on these sites, would increase the immunoreactivity of Scribble; 3) the epitope is masked by a protein that binds to it in the control cells, but this interaction is disrupted in CD74-overexpressing cells. The first model is immediately disproved because the SILAC analysis showed no significant change in total Scribble after 24 hours of tetracycline treatment. A Western blot analysis confirmed this (FIG. 3A), although in cells induced for longer periods of time Scribble abundance did decrease moderately (FIG. 9). Thus, CD74 overexpression increased the immunoreactivity of native Scribble but did not affect it in Western blots where the protein is fully unfolded and denatured. The Western blot results also disprove the second model: If increased Scribble immunoreactivity in the CD74-overexpressing cells was due to a hypophosphorylated epitope, it is likely that it would have shown up in the Western blot results as well. Thus, the only valid model is explanation 3, which assumes, for specific changes in the network of protein-protein interactions of Scribble, its immediate molecular microenvironment. This is consistent with the fact that Scribble appeared to change localization when CD74 was overexpressed (FIGS. 2 and 5).

Furthermore, when overexpressed CD74 was able to coimmunoprecipitate Scribble and was seen to colocalize with a subset of Scribble molecules (FIG. 4).

Taken together, our results show that when overexpressed, CD74 engages in a functional interaction with Scribble, which initially affects not only the total abundance of Scribble but also the pattern of its posttranslational modifications in the C-terminal part of the protein. This, by as yet to be elucidated mechanisms, causes the tumor suppressor protein to shift its localization from the basolateral membrane and the sites of cell-to-cell contacts to the cytoplasm and the apical membrane. Apparently, this also leads to a down-regulation of Scribble in the long run as the protein abundance decreased after 48 hours of induced CD74 expression (see FIG. 9). Thus, when CD74 is overexpressed for a prolonged period of time, it appears to cause an overall decrease in Scribble abundance. This is consistent with data from a large-scale LC-MS/MS analysis of a collection of breast tumors I carried out recently and will describe in a separate publication. In this data set, summarized in FIG. 10, CD74 and Scribble showed a clear negative correlation: The tumors with the highest CD74 abundance showed lowest Scribble abundance and vice versa. These data further corroborate the link between CD74 overexpression and Scribble deregulation established in our experiments with cell-based models and transient and stable inducible overexpression of CD74.

Scribble is a potential tumor suppressor and its deregulation and abnormal localization in breast tumors has been documented already [9]. The protein plays a crucial role in the maintenance of epithelial polarity [10,22,23]. It is known to interact with the mitogen-activated protein kinases of the ERK family, apparently downregulating their activation and ability to migrate to the nucleus [24,25]. As reported in the study of Nagasaka et al., in normal epithelial cells, Scribble is localized at the basolateral membrane and this is required for its ability to inhibit G1-to-S transition [26]. Here, I showed that overexpression of CD74, a frequently observed phenomenon in breast cancer, is a direct cause for deregulation of Scribble. This finding can explain why triple-negative breast tumors overexpressing CD74 tend to be more aggressive and with a heightened metastatic propensity. It also suggests that the pathway involved in this mechanism could be a good target for developing rationale-based therapies and companion diagnostics for the treatment of triple-negative breast cancer.

EXAMPLE II

Methods

1. Sample Preparation

Tumour tissue is collected as described previously [27] and kept frozen at −80° C. until needed for analysis. Membrane proteins are isolated by tissue permeabilization and detergent extraction as described in [27]. The isolated membrane proteins are digested with trypsin and the resulting peptide sample is quantified by spectrophotometry using a micro cuvette to minimize sample loss.

2. Detection and Quantification of the Biomarkers

The biomarkers are detected as positively-charged peptide ions by liquid chromatography and mass spectrometry. The a mass spectrometer should be capable of tandem mass analysis. I used an LTQ/Orbitrap Velos but other instruments can also be used. Prior to analysis, a cocktail of internal standards comprising stable isotope-labelled phosphorylated peptides might be added to the sample to be analysed. The internal standards have sequences identical to the Scribble peptides shown in Table 1, but are heavier by a precise number of mass units. This will allow precise absolute quantitation of the biomarker peptides. This type of analysis will generate similar data to the ones reported in Metodieva et al (2013). Alternatively or in addition, a relative quantitation can be performed, in which the intensity of the biomarker peptide ions, as measured by the mass spectrometer, would be normalized against the intensities of a panel of peptide ions generated by the ionization of select unmodified Scribble peptides.

Results

I have carried out model experiments with recombinant Scribble expressed in cultured human cells with the objective of confirming that the data obtained by analysing endogenous Scribble in large-scale quantitative phosphoproteomics in cancer cell lines is indeed accurate. This is very important as large-scale phosphoproteomics experiments can contain miss-assigned mass spectra, especially miss-assigned to phosphorylated sequences. To rule out any possibility that some of the results could have been generated through such miss-assignment I expressed epitope-tagged Scribble in human kidney embryonic cells (HEK293). I then affinity-purified the recombinant Scribble using a monoclonal antibody recognizing the epitope tag and confirmed the detection of the phosphorylated peptides. Then the four phosphorylation sites, S1306, S1309, S1348, and S1448 were mutagenized individually to Alanine to prevent the phosphorylation in vivo and the affinity purification experiment was carried again with cells expressing each of the 4 mutants. In each of these experiments only the peptides ions corresponding to the phosphorylation sites that were not mutagenized were detected but there were no peptides ions corresponding to the phosphorylation on the sites that were changed to Alanine. These results fully confirmed that the peptide ions I am measuring are indeed the 5 Scribble phosphopeptides listed in Table 1.

FIG. 11 illustrates the detection of one of the biomarkers in recombinant epitope-tagged Scribble purified from HEK293 cells. Specifically, the detection of phosphorylated peptide QSPAS(ph)PPPLGGGAPVR (SEQ ID NO:15) derived from human Scribble protein. The phosphorylation site was mapped to the serine residue at position 5 and is indicated with (ph) after the acceptor residue. The top trace is total ion chromatogram (TIC). Below is the base peak chromatogram trace in red. The phosphorylated peptide is detected as doubly-charged ion with a mass to charge ratio of 784.385. The extracted ion chromatogram for this peptide is shown as a blue trace. The isotopic cluster of this peptide ion is shown in the zoomed in high-resolution spectrum on the bottom. The unphosphorylated peptide was also detected as a doubly-charged ion with m/z of 744.402. Its extracted ion chromatogram is shown with a green trace and spectrum in the insert framed in blue.

TABLE 1

Scribble phosphopeptide biomarkers. The peptide sequences are shown with the phosphorylation sites indicated with (ph) after the acceptor residue. The peptide charges, mass to charge ratios, mass and mass error in ppm are also shown. The mass to charge ratios and masses are as determined by the Orbitrap analyser at resolution 30,000.

| Modified Sequence | Charge | m/z | Mass | Mass Error (ppm) | SEQ ID No. |
|---|---|---|---|---|---|
| AFAAVPTSHPPEDAPAQPPTPGPAAS(ph)PEQLSFR | 3 | 1140.208 | 3417.603 | −0.28113 | 11 |
| MAESPCSPSGQQPPS(ph)PPS(ph)PDEIPANVK | 3 | 988.7446 | 2963.212 | −0.20162 | 12 |
| MAESPCSPSGQQPPSPPS(ph)PDELPANVK | 3 | 962.0892 | 2883.246 | 0.02382 | 13 |
| MAESPCSPSGQQPPS(ph)PPSPDELPANVK | 3 | 962.0892 | 2883.246 | −0.12338 | 14 |
| QSPAS(ph)PPPLGGGAPVR | 2 | 784.3851 | 1566.756 | 0.28104 | 15 |

REFERENCES

[1] Burton J D, Ely S, Reddy P K, Stein R, Gold D V, Cardillo T M, and Goldenberg D M (2004). CD74 is expressed by multiple myeloma and is a promising target for therapy. Clin Cancer Res 10, 6606-6611.

[2] Gold D V, Stein R, Burton J, and Goldenberg D M (2010). Enhanced expression of CD74 in gastrointestinal cancers and benign tissues. Int J Clin Exp Pathol 4, 1-12.

[3] Sapra P, Stein R, Pickett J, Qu Z, Govindan S V, Cardillo T M, Hansen H J, Horak I D, Griffiths G L, and Goldenberg D M (2005). Anti-CD74 antibodydoxorubicin conjugate, IMMU-110, in a human multiple myeloma xenograft and in monkeys. Clin Cancer Res 11, 5257-5264.

[4] Leth-Larsen R, Lund R R, and Ditzel H J (2010). Plasma membrane proteomics and its application in clinical cancer biomarker discovery. Mol Cell Proteomics 9, 1369-1382.

[5] Greenwood C, Metodieva G, Al-Janabi K, Lausen B, Alldridge L, Leng L, Bucala R, Fernandez N, and Metodiev M V (2012). Stat1 and CD74 overexpression is co-dependent and linked to increased invasion and lymph node metastasis in triple-negative breast cancer. J Proteomics 75, 3031-3040.

[6] Leng L, Metz C N, Fang Y, Xu J, Donnelly S, Baugh J, Delohery T, Chen Y, Mitchell R A, and Bucala R (2003). MIF signal transduction initiated by binding to CD74. J Exp Med 197, 1467-1476.

[7] Lue H, Kapurniotu A, Fingerle-Rowson G, Roger T, Leng L, Thiele M, Calandra T, Bucala R, and Bernhagen J (2006). Rapid and transient activation of the ERK MAPK signalling pathway by macrophage migration inhibitory factor (MIF) and dependence on JAB1/CSN5 and Src kinase activity. Cell Signal 18, 688-703.

[8] Shi X, Leng L, Wang T, Wang W, Du X, Li J, McDonald C, Chen Z, Murphy J W, Lolis E, et al. (2006). CD44 is the signaling component of the macrophage migration inhibitory factor-CD74 receptor complex. Immunity 25, 595-606.

[9] Zhan L, Rosenberg A, Bergami K C, Yu M, Xuan Z, Jaffe A B, Allred C, and Muthuswamy S K (2008). Deregulation of Scribble promotes mammary tumorigenesis and reveals a role for cell polarity in carcinoma. Cell 135, 865-878.

[10] Bilder D and Perrimon N (2000). Localization of apical epithelial determinants by the basolateral PDZ protein Scribble. Nature 403, 676-680.

[11] Bilder D, Li M, and Perrimon N (2000). Cooperative regulation of cell polarity and growth by Drosophila tumor suppressors. Science 289, 113-116.

[12] Qin Y, Capaldo C, Gumbiner B M, and Macara I G (2005). The mammalian Scribble polarity protein regulates epithelial cell adhesion and migration through E-cadherin. J Cell Biol 171, 1061-1071.

[13] Ong S E, Blagoev B, Kratchmarova I, Kristensen D B, Steen H, Pandey A, and Mann M (2002). Stable isotope labeling by amino acids in cell culture, SILAC, as a simple and accurate approach to expression proteomics. Mol Cell Proteomics 1, 376-386.

[14] Reeves P J, Thurmond R L, and Khorana H G (1996). Structure and function in rhodopsin: high level expression of a synthetic bovine opsin gene and its mutants in stable mammalian cell lines. Proc Natl Acad Sci USA 93, 11487-11492.

[15] Alldridge L, Metodieva G, Greenwood C, Al-Janabi K, Thwaites L, Sauven P, and Metodiev M (2008). Proteome profiling of breast tumors by gel electrophoresis and nanoscale electrospray ionization mass spectrometry. J Proteome Res 7, 1458-1469.

[16] Cox J, Neuhauser N, Michalski A, Scheltema R A, Olsen J V, and Mann M (2011). Andromeda: a peptide search engine integrated into the MaxQuant environment. J Proteome Res 10, 1794-1805. [17] Luber C A, Cox J, Lauterbach H, Fancke B, Selbach M, Tschopp J, Akira S, Wiegand M, Hochrein H, O'Keeffe M, et al. (2010). Quantitative proteomics reveals subset-specific viral recognition in dendritic cells. Immunity 32, 279-289.

[18] Cox J and Mann M (2008). MaxQuant enables high peptide identification rates, individualized p.p.b.-range mass accuracies and proteome-wide protein quantification. Nat Biotechnol 26, 1367-1372.

[19] Olsen J V, Blagoev B, Gnad F, Macek B, Kumar C, Mortensen P, and Mann M (2006). Global, in vivo, and site-specific phosphorylation dynamics in signalling networks. Cell 127, 635-648.

[20] Beausoleil S A, Jedrychowski M, Schwartz D, Elias J E, Villen J, Li J, Cohn M A, Cantley L C, and Gygi S P (2004).

Large-scale characterization of HeLa cell nuclear phosphoproteins. Proc Natl Acad Sci USA 101, 12130-12135.

[21] Blagoev B, Kratchmarova I, Ong S E, Nielsen M, Foster L J, and Mann M (2003). A proteomics strategy to elucidate functional protein-protein interactions applied to EGF signaling. Nat Biotechnol 21, 315-318.

[22] Bilder D (2004). Epithelial polarity and proliferation control: links from the *Drosophila* neoplastic tumor suppressors. Genes Dev 18, 1909-1925.

[23] Bilder D, Schober M, and Perrimon N (2003). Integrated activity of PDZ protein complexes regulates epithelial polarity. Nat Cell Biol 5, 53-58.

[24] Nagasaka K, Massimi P, Pim D, Subbaiah V K, Kranjec C, Nakagawa S, Yano T, Taketani Y, and Banks L (2010). The mechanism and implications of hScrib regulation of ERK. Small GTPases 1, 108-112.

[25] Nagasaka K, Pim D, Massimi P, Thomas M, Tomaic V, Subbaiah V K, Kranjec C, Nakagawa S, Yano T, Taketani Y, et al. (2010). The cell polarity regulator hScrib controls ERK activation through a KIM site-dependent interaction. Oncogene 29, 5311-5321.

[26] Nagasaka K, Nakagawa S, Yano T, Takizawa S, Matsumoto Y, Tsuruga T, Nakagawa K, Minaguchi T, Oda K, Hiraike-Wada O, et al. (2006). Human homolog of *Drosophila* tumor suppressor Scribble negatively regulates cell-cycle progression from G1 to S phase by localizing at the basolateral membrane in epithelial cells. Cancer Sci 97, 1217-1225.

[27] Gergana Metodieva, Naiara Correa Nogueira-de-Souza, Christina Greenwood, Khalid Al-Janabi, Lin Leng, Richard Bucala, and Metodi V. Metodiev. 2013. CD74-dependent deregulation of the tumor suppressor Scribble in human epithelial and breast cancer cells. *Neoplasia*, 15(6), 660-668.

[28] Christian A. Luber, Jurgen Cox, Henning Lauterbach, Ben Fancke, Matthias Selbach, Jurg Tschopp, Shizuo Akira, Marian Wiegand, Hubertus Hochrein, Meredith O'Keeffe and Matthias Mann. 2010. Quantitative Proteomics Reveals Subset-Specific Viral Recognition in Dendritic Cells. *Immunity*. 32(2); 279-289.

The invention claimed is:

1. A method of treating cancer in a patient, the method comprising:
    detecting the phosphorylation status of one or more residues of a Scribble protein or fragment thereof, wherein the one or more residues are selected from the group consisting of S1306, S1309, S1348, and S1448 or a combination thereof; and
    administering a cancer treatment agent to the patient when said one or more residues of a Scribble protein or fragment thereof is unphosphorylated.

2. The method of claim 1, wherein the patient is a cancer patient or is at risk of developing cancer.

3. The method of claim 2, wherein the patient's cancer is an epithelial cancer.

4. The method of claim 3, wherein the patient's cancer is breast, pancreas, bone, liver, stomach, lung, colorectal, bladder, prostate or ovarian cancer.

5. The method of claim 4, wherein the cancer is breast cancer and wherein the breast cancer tumour does not express at least one marker selected from the group consisting of oestrogen receptor (ER), progesterone receptor (PgR) and the ErbB2 receptor.

6. The method of claim 1, wherein detecting the phosphorylation status comprises obtaining a sample from said patient and contacting the sample with at least one antibody that is capable of specifically binding phosphorylated or unphosphorylated residues of a Scribble protein or fragment thereof.

7. The method of claim 1, wherein detecting the phosphorylation status comprises obtaining a sample from said patient and detecting the phosphorylation status by mass spectrometry.

8. The method of claim 1, further comprising detecting the expression of one or more other biomarkers.

9. A method for treating a cancer patient, the method comprising:
    detecting the phosphorylation status of a Scribble protein of SEQ ID NO: 1, or fragment thereof, by
    obtaining a sample from a patient and contacting the sample with at least one antibody that is capable of specifically binding phosphorylated or unphosphorylated residues S1306, S1309, S1348 and S1448 or a combination thereof in the Scribble protein or fragment thereof; and
    administering to the patient a cancer treatment drug.

10. The method of claim 9, wherein the method is performed in conjunction with at least one of the following: evaluating cancer prognosis, developing a cancer treatment plan, assessing the efficiency of cancer treatment and the likelihood of metastases.

11. The method of claim 1, wherein the detecting step is performed with an antibody capable of selectively binding to at least one phosphorylated or unphosphorylated residue in a Scribble protein with SEQ ID NO: 1, or fragment or variant thereof, selected from residues S1306, S1309, S1348 and S1448 or a combination thereof.

12. The method of claim 1, wherein the detecting step is performed with a kit comprising at least one antibody capable of selectively binding to at least one phosphorylated or unphosphorylated residue in a Scribble protein with SEQ ID NO: 1, or fragment or variant thereof, selected from residues S1306, S1309, S1348 and S1448 or a combination thereof, wherein said kit further comprises agents for the detection of the at least one antibody binding to said phosphorylated residues in Scribble.

13. The method of claim 9, wherein the detecting step is performed with a kit comprising at least one antibody capable of selectively binding to at least one phosphorylated or unphosphorylated residue in a Scribble protein with SEQ ID NO: 1, or fragment or variant thereof, selected from residues S1306, S1309, S1348 and S1448 or a combination thereof, wherein said kit further comprises agents for the detection of the at least one antibody binding to said phosphorylated residues in Scribble.

* * * * *

```
SEQUENCE LISTING

<160> NUMBER OF SEQ ID NOS: 15

<210> SEQ ID NO 1
<211> LENGTH: 1630
<212> TYPE: PRT
<213> ORGANISM: Homo sapiens

<400> SEQUENCE: 1

Met Leu Lys Cys Ile Pro Leu Trp Arg Cys Asn Arg His Val Glu Ser
1               5                   10                  15

Val Asp Lys Arg His Cys Ser Leu Gln Ala Val Pro Glu Glu Ile Tyr
            20                  25                  30

Arg Tyr Ser Arg Ser Leu Glu Glu Leu Leu Leu Asp Ala Asn Gln Leu
        35                  40                  45

Arg Glu Leu Pro Lys Pro Phe Phe Arg Leu Leu Asn Leu Arg Lys Leu
    50                  55                  60

Gly Leu Ser Asp Asn Glu Ile Gln Arg Leu Pro Pro Glu Val Ala Asn
65                  70                  75                  80

Phe Met Gln Leu Val Glu Leu Asp Val Ser Arg Asn Asp Ile Pro Glu
                85                  90                  95

Ile Pro Glu Ser Ile Lys Phe Cys Lys Ala Leu Glu Ile Ala Asp Phe
            100                 105                 110

Ser Gly Asn Pro Leu Ser Arg Leu Pro Asp Gly Phe Thr Gln Leu Arg
        115                 120                 125

Ser Leu Ala His Leu Ala Leu Asn Asp Val Ser Leu Gln Ala Leu Pro
    130                 135                 140

Gly Asp Val Gly Asn Leu Ala Asn Leu Val Thr Leu Glu Leu Arg Glu
145                 150                 155                 160

Asn Leu Leu Lys Ser Leu Pro Ala Ser Leu Ser Phe Leu Val Lys Leu
                165                 170                 175

Glu Gln Leu Asp Leu Gly Gly Asn Asp Leu Glu Val Leu Pro Asp Thr
            180                 185                 190

Leu Gly Ala Leu Pro Asn Leu Arg Glu Leu Trp Leu Asp Arg Asn Gln
        195                 200                 205

Leu Ser Ala Leu Pro Pro Glu Leu Gly Asn Leu Arg Arg Leu Val Cys
    210                 215                 220
```

```
Leu Asp Val Ser Glu Asn Arg Leu Glu Glu Leu Pro Ala Glu Leu Gly
225                 230                 235                 240

Gly Leu Val Leu Leu Thr Asp Leu Leu Leu Ser Gln Asn Leu Leu Arg
            245                 250                 255

Arg Leu Pro Asp Gly Ile Gly Gln Leu Lys Gln Leu Ser Ile Leu Lys
        260                 265                 270

Val Asp Gln Asn Arg Leu Cys Glu Val Thr Glu Ala Ile Gly Asp Cys
    275                 280                 285

Glu Asn Leu Ser Glu Leu Ile Leu Thr Glu Asn Leu Leu Met Ala Leu
    290                 295                 300

Pro Arg Ser Leu Gly Lys Leu Thr Lys Leu Thr Asn Leu Asn Val Asp
305                 310                 315                 320

Arg Asn His Leu Glu Ala Leu Pro Pro Glu Ile Gly Gly Cys Val Ala
                325                 330                 335

Leu Ser Val Leu Ser Leu Arg Asp Asn Arg Leu Ala Val Leu Pro Pro
            340                 345                 350

Glu Leu Ala His Thr Thr Glu Leu His Val Leu Asp Val Ala Gly Asn
        355                 360                 365

Arg Leu Gln Ser Leu Pro Phe Ala Leu Thr His Leu Asn Leu Lys Ala
    370                 375                 380

Leu Trp Leu Ala Glu Asn Gln Ala Gln Pro Met Leu Arg Phe Gln Thr
385                 390                 395                 400

Glu Asp Asp Ala Arg Thr Gly Glu Lys Val Leu Thr Cys Tyr Leu Leu
                405                 410                 415

Pro Gln Gln Pro Pro Leu Ser Leu Glu Asp Ala Gly Gln Gln Gly Ser
            420                 425                 430

Leu Ser Glu Thr Trp Ser Asp Ala Pro Pro Ser Arg Val Ser Val Ile
        435                 440                 445

Gln Phe Leu Glu Ala Pro Ile Gly Asp Glu Asp Ala Glu Glu Ala Ala
    450                 455                 460

Ala Glu Lys Arg Gly Leu Gln Arg Arg Ala Thr Pro His Pro Ser Glu
465                 470                 475                 480

Leu Lys Val Met Lys Arg Ser Ile Glu Gly Arg Arg Ser Glu Ala Cys
                485                 490                 495

Pro Cys Gln Pro Asp Ser Gly Ser Pro Leu Pro Ala Glu Glu Glu Lys
            500                 505                 510

Arg Leu Ser Ala Glu Ser Gly Leu Ser Glu Asp Ser Arg Pro Ser Ala
        515                 520                 525

Ser Thr Val Ser Glu Ala Glu Pro Glu Gly Pro Ser Ala Glu Ala Gln
    530                 535                 540

Gly Gly Ser Gln Gln Glu Ala Thr Thr Ala Gly Gly Glu Glu Asp Ala
545                 550                 555                 560

Glu Glu Asp Tyr Gln Glu Pro Thr Val His Phe Ala Glu Asp Ala Leu
                565                 570                 575

Leu Pro Gly Asp Asp Arg Glu Ile Glu Gly Gln Pro Glu Ala Pro
            580                 585                 590

Trp Thr Leu Pro Gly Gly Arg Gln Arg Leu Ile Arg Lys Asp Thr Pro
        595                 600                 605

His Tyr Lys Lys His Phe Lys Ile Ser Lys Leu Pro Gln Pro Glu Ala
    610                 615                 620

Val Val Ala Leu Leu Gln Gly Met Gln Pro Asp Gly Glu Gly Pro Val
625                 630                 635                 640
```

-continued

Ala Pro Gly Gly Trp His Asn Gly Pro His Ala Pro Trp Ala Pro Arg
            645                 650                 655

Ala Gln Lys Glu Glu Glu Glu Glu Glu Gly Ser Pro Gln Glu Glu
        660                 665                 670

Glu Glu Glu Glu Glu Glu Asn Arg Ala Glu Glu Glu Ala Ser
        675                 680                 685

Thr Glu Glu Glu Asp Lys Gly Ala Val Val Ser Ala Pro Ser Val
    690                 695                 700

Lys Gly Val Ser Phe Asp Gln Ala Asn Asn Leu Leu Ile Glu Pro Ala
705                 710                 715                 720

Arg Ile Glu Glu Glu Leu Thr Leu Thr Ile Leu Arg Gln Thr Gly
                725                 730                 735

Gly Leu Gly Ile Ser Ile Ala Gly Gly Lys Gly Ser Thr Pro Tyr Lys
            740                 745                 750

Gly Asp Asp Glu Gly Ile Phe Ile Ser Arg Val Ser Glu Glu Gly Pro
    755                 760                 765

Ala Ala Arg Ala Gly Val Arg Val Gly Asp Lys Leu Leu Glu Val Asn
    770                 775                 780

Gly Val Ala Leu Gln Gly Ala Glu His His Glu Ala Val Glu Ala Leu
785                 790                 795                 800

Arg Gly Ala Gly Thr Ala Val Gln Met Arg Val Trp Arg Glu Arg Met
                805                 810                 815

Val Glu Pro Glu Asn Ala Val Thr Ile Thr Pro Leu Arg Pro Glu Asp
            820                 825                 830

Asp Tyr Ser Pro Arg Glu Arg Arg Gly Gly Gly Leu Arg Leu Pro Leu
    835                 840                 845

Leu Pro Pro Glu Ser Pro Gly Pro Leu Arg Gln Arg His Val Ala Cys
850                 855                 860

Leu Ala Arg Ser Glu Arg Gly Leu Gly Phe Ser Ile Ala Gly Gly Lys
865                 870                 875                 880

Gly Ser Thr Pro Tyr Arg Ala Gly Asp Ala Gly Ile Phe Val Ser Arg
                885                 890                 895

Ile Ala Glu Gly Gly Ala Ala His Arg Ala Gly Thr Leu Gln Val Gly
            900                 905                 910

Asp Arg Val Leu Ser Ile Asn Gly Val Asp Val Thr Glu Ala Arg His
        915                 920                 925

Asp His Ala Val Ser Leu Leu Thr Ala Ala Ser Pro Thr Ile Ala Leu
    930                 935                 940

Leu Leu Glu Arg Glu Ala Gly Gly Pro Leu Pro Pro Ser Pro Leu Pro
945                 950                 955                 960

His Ser Ser Pro Pro Thr Ala Ala Val Ala Thr Thr Ser Ile Thr Thr
                965                 970                 975

Ala Thr Pro Gly Val Pro Gly Leu Pro Ser Leu Ala Pro Ser Leu Leu
            980                 985                 990

Ala Ala Ala Leu Glu Gly Pro Tyr Pro Val Glu Glu Ile Arg Leu Pro
        995                 1000                1005

Arg Ala Gly Gly Pro Leu Gly Leu Ser Ile Val Gly Gly Ser Asp
    1010                1015                1020

His Ser Ser His Pro Phe Gly Val Gln Glu Pro Gly Val Phe Ile
    1025                1030                1035

Ser Lys Val Leu Pro Arg Gly Leu Ala Ala Arg Ser Gly Leu Arg
    1040                1045                1050

```
Val Gly Asp Arg Ile Leu Ala Val Asn Gly Gln Asp Val Arg Asp
1055                1060                1065

Ala Thr His Gln Glu Ala Val Ser Ala Leu Leu Arg Pro Cys Leu
1070                1075                1080

Glu Leu Ser Leu Leu Val Arg Arg Asp Pro Ala Pro Pro Gly Leu
1085                1090                1095

Arg Glu Leu Cys Ile Gln Lys Ala Pro Gly Glu Arg Leu Gly Ile
1100                1105                1110

Ser Ile Arg Gly Gly Ala Arg Gly His Ala Gly Asn Pro Arg Asp
1115                1120                1125

Pro Thr Asp Glu Gly Ile Phe Ile Ser Lys Val Ser Pro Thr Gly
1130                1135                1140

Ala Ala Gly Arg Asp Gly Arg Leu Arg Val Gly Leu Arg Leu Leu
1145                1150                1155

Glu Val Asn Gln Gln Ser Leu Leu Gly Leu Thr His Gly Glu Ala
1160                1165                1170

Val Gln Leu Leu Arg Ser Val Gly Asp Thr Leu Thr Val Leu Val
1175                1180                1185

Cys Asp Gly Phe Glu Ala Ser Thr Asp Ala Ala Leu Glu Val Ser
1190                1195                1200

Pro Gly Val Ile Ala Asn Pro Phe Ala Ala Gly Ile Gly His Arg
1205                1210                1215

Asn Ser Leu Glu Ser Ile Ser Ser Ile Asp Arg Glu Leu Ser Pro
1220                1225                1230

Glu Gly Pro Gly Lys Glu Lys Glu Leu Pro Gly Gln Thr Leu His
1235                1240                1245

Trp Gly Pro Glu Ala Thr Glu Ala Ala Gly Arg Gly Leu Gln Pro
1250                1255                1260

Leu Lys Leu Asp Tyr Arg Ala Leu Ala Ala Val Pro Ser Ala Gly
1265                1270                1275

Ser Val Gln Arg Val Pro Ser Gly Ala Ala Gly Gly Lys Met Ala
1280                1285                1290

Glu Ser Pro Cys Ser Pro Ser Gly Gln Gln Pro Pro Ser Pro Pro
1295                1300                1305

Ser Pro Asp Glu Leu Pro Ala Asn Val Lys Gln Ala Tyr Arg Ala
1310                1315                1320

Phe Ala Ala Val Pro Thr Ser His Pro Pro Glu Asp Ala Pro Ala
1325                1330                1335

Gln Pro Pro Thr Pro Gly Pro Ala Ala Ser Pro Glu Gln Leu Ser
1340                1345                1350

Phe Arg Glu Arg Gln Lys Tyr Phe Glu Leu Glu Val Arg Val Pro
1355                1360                1365

Gln Ala Glu Gly Pro Pro Lys Arg Val Ser Leu Val Gly Ala Asp
1370                1375                1380

Asp Leu Arg Lys Met Gln Glu Glu Ala Arg Lys Leu Gln Gln
1385                1390                1395

Lys Arg Ala Gln Met Leu Arg Glu Ala Ala Glu Ala Gly Ala Glu
1400                1405                1410

Ala Arg Leu Ala Leu Asp Gly Glu Thr Leu Gly Glu Glu Glu Gln
1415                1420                1425

Glu Asp Glu Gln Pro Pro Trp Ala Ser Pro Ser Pro Thr Ser Arg
1430                1435                1440
```

```
Gln Ser Pro Ala Ser Pro Pro Pro Leu Gly Gly Gly Ala Pro Val
    1445                1450                1455

Arg Thr Ala Lys Ala Glu Arg His Gln Glu Arg Leu Arg Val
    1460                1465                1470

Gln Ser Pro Glu Pro Pro Ala Pro Glu Arg Ala Leu Ser Pro Ala
    1475                1480                1485

Lys Leu Arg Ala Leu Glu Ala Lys Arg Ala Leu Trp Arg Ala
    1490                1495                1500

Ala Arg Met Lys Ser Leu Glu Gln Asp Ala Leu Arg Ala Gln Met
    1505                1510                1515

Val Leu Ser Arg Ser Gln Gly Arg Gly Thr Arg Gly Pro Leu
    1520                1525                1530

Glu Arg Leu Ala Glu Ala Pro Ser Pro Ala Pro Thr Pro Ser Pro
    1535                1540                1545

Thr Pro Val Glu Asp Leu Gly Pro Gln Thr Ser Thr Ser Pro Gly
    1550                1555                1560

Arg Leu Ser Pro Asp Phe Ala Glu Glu Leu Arg Ser Leu Glu Pro
    1565                1570                1575

Ser Pro Ser Pro Gly Pro Gln Glu Glu Asp Gly Glu Val Ala Leu
    1580                1585                1590

Val Leu Leu Gly Arg Pro Ser Pro Gly Ala Val Gly Pro Glu Asp
    1595                1600                1605

Val Ala Leu Cys Ser Ser Arg Arg Pro Val Arg Pro Gly Arg Arg
    1610                1615                1620

Gly Leu Gly Pro Val Pro Ser
    1625                1630

<210> SEQ ID NO 2
<211> LENGTH: 33
<212> TYPE: DNA
<213> ORGANISM: Artificial Sequence
<220> FEATURE:
<223> OTHER INFORMATION: CD74 primer sequence

<400> SEQUENCE: 2
ggaattcgcc accatgcaca ggaggagaag cag                                33

<210> SEQ ID NO 3
<211> LENGTH: 33
<212> TYPE: DNA
<213> ORGANISM: Artificial Sequence
<220> FEATURE:
<223> OTHER INFORMATION: CD74 primer sequence

<400> SEQUENCE: 3
gcggccgctc acatggggac tgggcccaga tcc                                33

<210> SEQ ID NO 4
<211> LENGTH: 10
<212> TYPE: PRT
<213> ORGANISM: Homo sapiens

<400> SEQUENCE: 4

Val Ser Leu Val Gly Ala Asp Asp Leu Arg
1               5                   10

<210> SEQ ID NO 5
<211> LENGTH: 11
<212> TYPE: PRT
<213> ORGANISM: Homo sapiens
```

```
<400> SEQUENCE: 5

Val Gln Ser Pro Glu Pro Pro Ala Pro Glu Arg
1               5                   10

<210> SEQ ID NO 6
<211> LENGTH: 26
<212> TYPE: PRT
<213> ORGANISM: Homo sapiens

<400> SEQUENCE: 6

Met Ala Glu Ser Pro Cys Ser Pro Ser Gly Gln Gln Pro Pro Ser Pro
1               5                   10                  15

Pro Ser Pro Asp Glu Ile Pro Ala Asn Val
            20                  25

<210> SEQ ID NO 7
<211> LENGTH: 27
<212> TYPE: PRT
<213> ORGANISM: Homo sapiens

<400> SEQUENCE: 7

Met Ala Glu Ser Pro Cys Ser Pro Ser Gly Gln Gln Pro Pro Ser Pro
1               5                   10                  15

Pro Ser Pro Asp Glu Ile Pro Ala Asn Val Lys
            20                  25

<210> SEQ ID NO 8
<211> LENGTH: 33
<212> TYPE: PRT
<213> ORGANISM: Homo sapiens

<400> SEQUENCE: 8

Ala Phe Ala Ala Val Pro Thr Ser His Pro Pro Glu Asp Ala Pro Ala
1               5                   10                  15

Gln Pro Pro Thr Pro Gly Pro Ala Ala Ser Pro Glu Gln Ile Ser Phe
            20                  25                  30

Arg

<210> SEQ ID NO 9
<211> LENGTH: 16
<212> TYPE: PRT
<213> ORGANISM: Homo sapiens

<400> SEQUENCE: 9

Gln Ser Pro Ala Ser Pro Pro Ile Gly Gly Gly Ala Pro Val Arg
1               5                   10                  15

<210> SEQ ID NO 10
<211> LENGTH: 1620
<212> TYPE: PRT
<213> ORGANISM: Homo sapiens

<400> SEQUENCE: 10

Met Leu Lys Cys Ile Pro Leu Trp Arg Cys Asn Arg His Val Glu Ser
1               5                   10                  15

Val Asp Lys Arg His Cys Ser Leu Gln Ala Val Pro Glu Glu Ile Tyr
            20                  25                  30

Arg Tyr Ser Arg Ser Leu Glu Glu Leu Leu Asp Ala Asn Gln Leu
        35                  40                  45
```

```
Arg Glu Leu Pro Lys Pro Phe Phe Arg Leu Leu Asn Leu Arg Lys Leu
 50                  55                  60

Gly Leu Ser Asp Asn Glu Ile Gln Arg Leu Pro Pro Glu Val Ala Asn
 65                  70                  75                  80

Phe Met Gln Leu Val Glu Leu Asp Val Ser Arg Asn Asp Ile Pro Glu
                 85                  90                  95

Ile Pro Glu Ser Ile Lys Phe Cys Lys Ala Leu Glu Ile Ala Asp Phe
            100                 105                 110

Ser Gly Asn Pro Leu Ser Arg Leu Pro Asp Gly Phe Thr Gln Leu Arg
            115                 120                 125

Ser Leu Ala His Leu Ala Leu Asn Asp Val Ser Leu Gln Ala Leu Pro
130                 135                 140

Gly Asp Val Gly Asn Leu Ala Asn Leu Val Thr Leu Glu Leu Arg Glu
145                 150                 155                 160

Asn Leu Leu Lys Ser Leu Pro Ala Ser Leu Ser Phe Leu Val Lys Leu
                165                 170                 175

Glu Gln Leu Asp Leu Gly Gly Asn Asp Leu Glu Val Leu Pro Asp Thr
            180                 185                 190

Leu Gly Ala Leu Pro Asn Leu Arg Glu Leu Trp Leu Asp Arg Asn Gln
            195                 200                 205

Leu Ser Ala Leu Pro Pro Glu Leu Gly Asn Leu Arg Arg Leu Val Cys
210                 215                 220

Leu Asp Val Ser Glu Asn Arg Leu Glu Glu Leu Pro Ala Glu Leu Gly
225                 230                 235                 240

Gly Leu Val Leu Leu Thr Asp Leu Leu Leu Ser Gln Asn Leu Leu Arg
                245                 250                 255

Arg Leu Pro Asp Gly Ile Gly Gln Leu Lys Gln Leu Ser Ile Leu Lys
            260                 265                 270

Val Asp Gln Asn Arg Leu Cys Glu Val Thr Glu Ala Ile Gly Asp Cys
            275                 280                 285

Glu Asn Leu Ser Glu Leu Ile Leu Thr Glu Asn Leu Leu Met Ala Leu
290                 295                 300

Pro Arg Ser Leu Gly Lys Leu Thr Lys Leu Thr Asn Leu Asn Val Asp
305                 310                 315                 320

Arg Asn His Leu Glu Ala Leu Pro Pro Glu Ile Gly Gly Cys Val Ala
                325                 330                 335

Leu Ser Val Leu Ser Leu Arg Asp Asn Arg Leu Ala Val Leu Pro Pro
            340                 345                 350

Glu Leu Ala His Thr Thr Glu Leu His Val Leu Asp Val Ala Gly Asn
            355                 360                 365

Arg Leu Gln Ser Leu Pro Phe Ala Leu Thr His Leu Asn Leu Lys Ala
370                 375                 380

Leu Trp Leu Ala Glu Asn Gln Ala Gln Pro Met Leu Arg Phe Gln Thr
385                 390                 395                 400

Glu Asp Asp Ala Arg Thr Gly Glu Lys Val Leu Thr Cys Tyr Leu Leu
                405                 410                 415

Pro Gln Gln Pro Pro Ser Leu Glu Asp Ala Gly Gln Gln Gly Ser
            420                 425                 430

Leu Ser Glu Thr Trp Ser Asp Ala Pro Pro Ser Arg Val Ser Val Ile
            435                 440                 445

Gln Phe Leu Glu Ala Pro Ile Gly Asp Glu Asp Ala Glu Glu Ala Ala
            450                 455                 460
```

-continued

```
Ala Glu Lys Arg Gly Leu Gln Arg Arg Ala Thr Pro His Pro Ser Glu
465                 470                 475                 480

Leu Lys Val Met Lys Arg Ser Ile Glu Gly Arg Arg Ser Glu Ala Cys
            485                 490                 495

Pro Cys Gln Pro Asp Ser Gly Ser Pro Leu Pro Ala Glu Glu Glu Lys
        500                 505                 510

Arg Leu Ser Ala Glu Ser Gly Leu Ser Glu Asp Ser Arg Pro Ser Ala
    515                 520                 525

Ser Thr Val Ser Glu Ala Glu Pro Glu Gly Pro Ser Ala Glu Ala Gln
    530                 535                 540

Gly Gly Ser Gln Gln Glu Ala Thr Thr Ala Gly Gly Glu Glu Asp Ala
545                 550                 555                 560

Glu Glu Asp Tyr Gln Glu Pro Thr Val His Phe Ala Glu Asp Ala Leu
            565                 570                 575

Leu Pro Gly Asp Asp Arg Glu Ile Glu Gly Gln Pro Glu Ala Pro
            580                 585                 590

Trp Thr Leu Pro Gly Gly Arg Gln Arg Leu Ile Arg Lys Asp Thr Pro
            595                 600                 605

His Tyr Lys Lys His Phe Lys Ile Ser Lys Leu Pro Gln Pro Glu Ala
            610                 615                 620

Val Val Ala Leu Leu Gln Gly Met Gln Pro Asp Gly Glu Gly Pro Val
625                 630                 635                 640

Ala Pro Gly Gly Trp His Asn Gly Pro His Ala Pro Trp Ala Pro Arg
                645                 650                 655

Ala Gln Lys Glu Glu Glu Glu Glu Glu Gly Ser Pro Gln Glu Glu
            660                 665                 670

Glu Val Glu Glu Glu Glu Asn Arg Ala Glu Glu Glu Ala Ser
            675                 680                 685

Thr Glu Glu Glu Asp Lys Glu Gly Ala Val Val Ser Ala Pro Ser Val
    690                 695                 700

Lys Gly Val Ser Phe Asp Gln Ala Asn Asn Leu Leu Ile Glu Pro Ala
705                 710                 715                 720

Arg Ile Glu Glu Glu Glu Leu Thr Leu Thr Ile Leu Arg Gln Thr Gly
                725                 730                 735

Gly Leu Gly Ile Ser Ile Ala Gly Gly Lys Gly Ser Thr Pro Tyr Lys
            740                 745                 750

Gly Asp Asp Glu Gly Ile Phe Ile Ser Arg Val Ser Glu Glu Gly Pro
        755                 760                 765

Ala Ala Arg Ala Gly Val Arg Val Gly Asp Lys Leu Leu Glu Val Asn
    770                 775                 780

Gly Val Ala Leu Gln Gly Ala Glu His His Glu Ala Val Glu Ala Leu
785                 790                 795                 800

Arg Gly Ala Gly Thr Ala Val Gln Met Arg Val Trp Arg Glu Arg Met
                805                 810                 815

Val Glu Pro Glu Asn Ala Val Thr Ile Thr Pro Leu Arg Pro Glu Asp
            820                 825                 830

Asp Tyr Ser Pro Arg Glu Arg Gly Gly Gly Leu Arg Leu Pro Leu
        835                 840                 845

Leu Pro Pro Glu Ser Pro Gly Pro Leu Arg Gln Arg His Val Ala Cys
    850                 855                 860

Leu Ala Arg Ser Glu Arg Gly Leu Gly Phe Ser Ile Ala Gly Gly Lys
865                 870                 875                 880
```

-continued

```
Gly Ser Thr Pro Tyr Arg Ala Gly Asp Ala Gly Ile Phe Val Ser Arg
            885                 890                 895

Ile Ala Glu Gly Gly Ala Ala His Arg Ala Gly Thr Leu Gln Val Gly
        900                 905                 910

Asp Arg Val Leu Ser Ile Asn Gly Val Asp Val Thr Glu Ala Arg His
        915                 920                 925

Asp His Ala Val Ser Leu Leu Thr Ala Ala Ser Pro Thr Ile Ala Leu
    930                 935                 940

Leu Leu Glu Arg Glu Ala Gly Gly Pro Leu Pro Ser Pro Leu Pro
945                 950                 955                 960

His Ser Ser Pro Pro Thr Ala Val Ala Thr Thr Ser Ile Thr Thr
            965                 970                 975

Ala Thr Pro Gly Val Pro Gly Leu Pro Ser Leu Ala Pro Ser Leu Leu
            980                 985                 990

Ala Ala Ala Leu Glu Gly Pro Tyr Pro Val Glu Glu Ile Arg Leu Pro
        995                 1000                1005

Arg Ala Gly Gly Pro Leu Gly Leu Ser Ile Val Gly Gly Ser Asp
    1010                1015                1020

His Ser Ser His Pro Phe Gly Val Gln Glu Pro Gly Val Phe Ile
    1025                1030                1035

Ser Lys Val Leu Pro Arg Gly Leu Ala Ala Arg Ser Gly Leu Arg
    1040                1045                1050

Val Gly Asp Arg Ile Leu Ala Val Asn Gly Gln Asp Val Arg Asp
    1055                1060                1065

Ala Thr His Gln Glu Ala Val Ser Ala Leu Leu Arg Pro Cys Leu
    1070                1075                1080

Glu Leu Ser Leu Leu Val Arg Arg Asp Pro Ala Pro Pro Gly Leu
    1085                1090                1095

Arg Glu Leu Cys Ile Gln Lys Ala Pro Gly Glu Arg Leu Gly Ile
    1100                1105                1110

Ser Ile Arg Gly Gly Ala Arg Gly His Ala Gly Asn Pro Arg Asp
    1115                1120                1125

Pro Thr Asp Glu Gly Ile Phe Ile Ser Lys Val Ser Pro Thr Gly
    1130                1135                1140

Ala Ala Gly Arg Asp Gly Arg Leu Arg Val Gly Leu Arg Leu Leu
    1145                1150                1155

Glu Val Asn Gln Gln Ser Leu Leu Gly Leu Thr His Gly Glu Ala
    1160                1165                1170

Val Gln Leu Leu Arg Ser Val Gly Asp Thr Leu Thr Val Leu Val
    1175                1180                1185

Cys Asp Gly Phe Glu Ala Ser Thr Asp Ala Ala Leu Glu Val Ser
    1190                1195                1200

Pro Gly Val Ile Ala Asn Pro Phe Ala Ala Gly Ile Gly His Arg
    1205                1210                1215

Asn Ser Leu Glu Ser Ile Ser Ser Ile Asp Arg Glu Leu Ser Pro
    1220                1225                1230

Glu Gly Pro Gly Lys Glu Lys Glu Leu Pro Gly Gln Thr Leu His
    1235                1240                1245

Trp Gly Pro Glu Ala Thr Glu Ala Ala Gly Arg Gly Leu Gln Pro
    1250                1255                1260

Leu Lys Leu Asp Tyr Arg Ala Leu Ala Ala Val Pro Ser Ala Gly
    1265                1270                1275
```

```
Ser Val Gln Arg Val Pro Ser Gly Ala Ala Gly Gly Lys Met Ala
    1280                1285                1290

Glu Ser Pro Cys Ser Pro Ser Gly Gln Gln Pro Pro Ser Pro Pro
    1295                1300                1305

Ser Pro Asp Glu Leu Pro Ala Asn Val Lys Gln Ala Tyr Arg Ala
    1310                1315                1320

Phe Ala Ala Val Pro Thr Ser His Pro Pro Glu Asp Ala Pro Ala
    1325                1330                1335

Gln Pro Pro Thr Pro Gly Pro Ala Ala Ser Pro Glu Gln Leu Ser
    1340                1345                1350

Phe Arg Glu Arg Gln Lys Tyr Phe Glu Leu Glu Val Arg Val Pro
    1355                1360                1365

Gln Ala Glu Gly Pro Pro Lys Arg Val Ser Leu Val Gly Ala Asp
    1370                1375                1380

Asp Leu Arg Lys Met Gln Glu Glu Ala Arg Lys Leu Gln Gln
    1385                1390                1395

Lys Arg Ala Gln Met Leu Arg Glu Ala Ala Glu Ala Gly Ala Glu
    1400                1405                1410

Ala Arg Leu Ala Leu Asp Gly Glu Thr Leu Gly Glu Glu Glu Gln
    1415                1420                1425

Glu Asp Glu Gln Pro Pro Trp Ala Ser Pro Ser Pro Thr Ser Arg
    1430                1435                1440

Gln Ser Pro Ala Ser Pro Pro Leu Gly Gly Gly Ala Pro Val
    1445                1450                1455

Arg Thr Ala Lys Ala Glu Arg Arg His Gln Glu Arg Leu Arg Val
    1460                1465                1470

Gln Ser Pro Glu Pro Pro Ala Pro Glu Arg Ala Leu Ser Pro Ala
    1475                1480                1485

Glu Leu Arg Ala Leu Glu Ala Glu Lys Arg Ala Leu Trp Arg Ala
    1490                1495                1500

Ala Arg Met Lys Ser Leu Glu Gln Asp Ala Leu Arg Ala Gln Met
    1505                1510                1515

Val Leu Ser Arg Ser Gln Glu Gly Arg Gly Thr Arg Gly Pro Leu
    1520                1525                1530

Glu Arg Leu Ala Glu Ala Pro Ser Pro Ala Pro Thr Pro Ser Pro
    1535                1540                1545

Thr Pro Val Glu Asp Leu Gly Pro Gln Thr Ser Thr Ser Pro Gly
    1550                1555                1560

Arg Leu Ser Pro Asp Phe Ala Glu Glu Leu Arg Ser Leu Glu Pro
    1565                1570                1575

Ser Pro Ser Pro Gly Pro Gln Glu Glu Asp Gly Glu Val Ala Leu
    1580                1585                1590

Val Leu Leu Gly Arg Pro Ser Pro Gly Ala Val Gly Pro Glu Asp
    1595                1600                1605

Val Ala Leu Cys Ser Ser Arg Arg Pro Val Arg Pro
    1610                1615                1620

<210> SEQ ID NO 11
<211> LENGTH: 33
<212> TYPE: PRT
<213> ORGANISM: Homo sapiens
<220> FEATURE:
<221> NAME/KEY: misc_feature
<222> LOCATION: (26)..(26)
<223> OTHER INFORMATION: phosphorylation site
```

-continued

```
<400> SEQUENCE: 11

Ala Phe Ala Ala Val Pro Thr Ser His Pro Pro Glu Asp Ala Pro Ala
1               5                   10                  15

Gln Pro Pro Thr Pro Gly Pro Ala Ala Ser Pro Glu Gln Leu Ser Phe
            20                  25                  30

Arg

<210> SEQ ID NO 12
<211> LENGTH: 27
<212> TYPE: PRT
<213> ORGANISM: Homo sapiens
<220> FEATURE:
<221> NAME/KEY: misc_feature
<222> LOCATION: (15)..(15)
<223> OTHER INFORMATION: phosphorylation site
<220> FEATURE:
<221> NAME/KEY: misc_feature
<222> LOCATION: (18)..(18)
<223> OTHER INFORMATION: phosphorylation site

<400> SEQUENCE: 12

Met Ala Glu Ser Pro Cys Ser Pro Ser Gly Gln Gln Pro Pro Ser Pro
1               5                   10                  15

Pro Ser Pro Asp Glu Ile Pro Ala Asn Val Lys
            20                  25

<210> SEQ ID NO 13
<211> LENGTH: 27
<212> TYPE: PRT
<213> ORGANISM: Homo sapiens
<220> FEATURE:
<221> NAME/KEY: misc_feature
<222> LOCATION: (18)..(18)
<223> OTHER INFORMATION: phosphorylation site

<400> SEQUENCE: 13

Met Ala Glu Ser Pro Cys Ser Pro Ser Gly Gln Gln Pro Pro Ser Pro
1               5                   10                  15

Pro Ser Pro Asp Glu Leu Pro Ala Asn Val Lys
            20                  25

<210> SEQ ID NO 14
<211> LENGTH: 27
<212> TYPE: PRT
<213> ORGANISM: Homo sapiens
<220> FEATURE:
<221> NAME/KEY: misc_feature
<222> LOCATION: (15)..(15)
<223> OTHER INFORMATION: phosphorylation site

<400> SEQUENCE: 14

Met Ala Glu Ser Pro Cys Ser Pro Ser Gly Gln Gln Pro Pro Ser Pro
1               5                   10                  15

Pro Ser Pro Asp Glu Leu Pro Ala Asn Val Lys
            20                  25

<210> SEQ ID NO 15
<211> LENGTH: 16
<212> TYPE: PRT
<213> ORGANISM: Homo sapiens
<220> FEATURE:
<221> NAME/KEY: misc_feature
<222> LOCATION: (5)..(5)
<223> OTHER INFORMATION: phosphorylation site
```

```
<400> SEQUENCE: 15

Gln Ser Pro Ala Ser Pro Pro Pro Leu Gly Gly Gly Ala Pro Val Arg
1               5                   10                  15
```